US009463266B2

(12) United States Patent
Noguchi et al.

(10) Patent No.: US 9,463,266 B2
(45) Date of Patent: Oct. 11, 2016

(54) PREPARATION APPARATUS AND PREPARATION METHOD FOR DIALYSIS FLUID OF VARIABLE BICARBONATE ION CONCENTRATION TYPE, DIALYSATE OF VARIABLE BICARBONATE ION CONCENTRATION TYPE, AND DIALYSIS SYSTEM OF VARIABLE BICARBONATE ION CONCENTRATION TYPE

(71) Applicant: Tomita Pharmaceutical Co., Ltd., Tokushima (JP)

(72) Inventors: Hiroshi Noguchi, Tokushima (JP);
Junya Kikuishi, Tokushima (JP);
Hideyuki Aoyama, Tokushima (JP);
Mina Hashimoto, Tokushima (JP)

(73) Assignee: Tomita Pharmaceuticals Co., Ltd., Tokushima (JP)

( * ) Notice: Subject to any disclaimer, the term of this patent is extended or adjusted under 35 U.S.C. 154(b) by 622 days.

(21) Appl. No.: 13/728,257

(22) Filed: Dec. 27, 2012

(65) Prior Publication Data

US 2013/0168316 A1  Jul. 4, 2013

(30) Foreign Application Priority Data

Dec. 29, 2011 (JP) .................................. 2011-290339
Apr. 27, 2012 (JP) .................................. 2012-103963

(51) Int. Cl.
*A61M 1/16* (2006.01)
*B01D 61/26* (2006.01)

(52) U.S. Cl.
CPC ......... *A61M 1/1656* (2013.01); *A61M 1/1654* (2013.01); *A61M 1/1666* (2014.02); *Y10T 137/2499* (2015.04)

(58) Field of Classification Search
CPC A61K 33/10; A61M 1/1654; A61M 1/1656; A61M 1/1666; Y10T 137/2499
See application file for complete search history.

(56) References Cited

U.S. PATENT DOCUMENTS 4,655,941 A * 4/1987 Suzuki ..................... A61K 9/14
159/48.1
5,318,750 A * 6/1994 Lascombes ..................... 422/81
(Continued)

FOREIGN PATENT DOCUMENTS

EP         0597817 A2 *  5/1994
JP         H04-075017 B2  9/1987
(Continued)

*Primary Examiner* — John Kim
(74) *Attorney, Agent, or Firm* — Knobbe, Martens, Olson & Bear, LLP

(57) ABSTRACT

Technology for preparing a dialysis fluid capable of flexibly changing bicarbonate ion concentration and maintaining concentrations of electrolytes such as potassium, calcium, and magnesium at constant levels during dialysis according to the disease state of a patient. A three-component dialysate containing an agent S containing sodium chloride, an agent B containing sodium bicarbonate, and an agent A containing electrolyte components other than sodium chloride and sodium bicarbonate, with suitable adjustment of the amount of the agent B during dialysis fluid preparation maintains concentrations of trace metal ions such as potassium ions, calcium ions, and magnesium ions in a dialysis fluid at constant levels and flexibly changes the bicarbonate ion concentration therein. Adjusting the ratio between the amount of the agent S and agent B when the dialysate is used also makes it possible to maintain the sodium ion concentration at a constant level or flexibly change the sodium ion concentration.

14 Claims, 5 Drawing Sheets

(56) References Cited

U.S. PATENT DOCUMENTS

| | | |
|---|---|---|
| 5,616,248 A | 4/1997 | Schal |
| 6,428,706 B1 * | 8/2002 | Rosenqvist et al. .......... 210/646 |
| 7,387,734 B2 | 6/2008 | Felding |
| 2006/0191850 A1 | 8/2006 | Bosetto et al. |
| 2006/0237351 A1 | 10/2006 | Felding |

FOREIGN PATENT DOCUMENTS

| | | |
|---|---|---|
| JP | H06-245995 A | 9/1993 |
| JP | 3586767 | 11/2004 |
| JP | 2005-198943 A | 7/2005 |
| JP | 4235555 B2 | 12/2008 |

* cited by examiner

PREPARATION APPARATUS AND PREPARATION METHOD FOR DIALYSIS FLUID OF VARIABLE BICARBONATE ION CONCENTRATION TYPE, DIALYSATE OF VARIABLE BICARBONATE ION CONCENTRATION TYPE, AND DIALYSIS SYSTEM OF VARIABLE BICARBONATE ION CONCENTRATION TYPE

CROSS-REFERENCE TO RELATED APPLICATIONS

This application claims the benefit of priority to Japanese Patent Application No. 2011-290339, filed Dec. 29, 2011 and to Japanese Patent Application No. 2012-103963, filed Apr. 27, 2012, each of which is incorporated by reference in its entirety herein.

BACKGROUND

1. Field

One embodiment of the present invention relates to a dialysate for preparing a dialysis fluid in which the concentrations of trace metal ions such as potassium ions, calcium ions, and magnesium ions can be maintained at constant levels and the bicarbonate concentration can be suitably changed according to the disease state of a patient. Moreover, one embodiment of the present invention relates to a method and an apparatus for preparing such a dialysis fluid. One embodiment of the present invention relates to a dialysis system that uses such a dialysis fluid and an apparatus.

2. Description of the Related Art

Hemodialysis intended for patients with renal failure is widely performed to remove wastes such as electrolytes and uremic toxins present in patient's blood via a dialyzer based mainly on the principle of diffusion or the like, generally using a dialysis fluid obtained by dissolving/diluting a fluid A (agent A) that contains electrolyte components and a fluid B (agent B) that contains sodium bicarbonate with purified water called RO water that has passed through a reverse osmosis membrane or the like.

The fluid A is provided as a concentrate or powder and often dissolved in RO water when used, and the fluid B also is provided as a concentrate or powder and often dissolved in RO water when used.

The component concentrations of an ordinary bicarbonate dialysis fluid are presented below. Bicarbonate dialysis fluids are roughly classified into acetate ion-containing dialysis fluids and dialysis fluids that do not contain acetate ions, i.e., acetate-free. Practically, bicarbonate dialysis fluids often do not contain citrate ions when containing acetate ions, and do not contain acetate ions when containing citrate ions.

Sodium ions: 120 to 150 mEq/l
Potassium ions: 0.5 to 3.0 mEq/l
Calcium ions: 1.5 to 4.5 mEq/l
Magnesium ions: 0 to 2.0 mEq/l
Chloride ions: 90 to 135 mEq/l
Bicarbonate ions: 20 to 40 mEq/l
Acetate ions: 0 to 12 mEq/l
Citrate ions: 0 to 18 mEq/l
Lactate ions: 0 to 10 mEq/l
Malate ions: 0 to 10 mEq/l
Gluconate ions: 0 to 10 mEq/l
Succinate ions: 0 to 10 mEq/l
Glucose: 0 to 2.5 g/l Although it is seldom used in Japan now, a formulation called an acetate dialysate was also used in the past, and the widely used acetate dialysate contained neither bicarbonate ions nor citrate ions but 30 to 42.5 mEq/l of acetate ions, and the compositions of other components were the same as those in the aforementioned bicarbonate dialysis fluid (see JP H4-75017B, hereafter referred to as "Patent Literature 1"). Meanwhile, in peritoneal dialysis, the dialysis fluid does not contain potassium ions, and lactic acid, sodium lactate, and the like are used as a pH adjuster and an alkaline agent.

Dialysis fluids have the above-described history, and hemodialysis fluids for use particularly in patients with renal failure in Japan are often produced as follows. A powdery agent A generally containing electrolyte components is dissolved in water to give a concentrated fluid A, a powdery agent B composed of sodium bicarbonate is dissolved in water to give a concentrated fluid B, and the concentrated fluids A and B are mixed/diluted in a ratio of fluid A:fluid B:RO water=1:1.26:32.74 using a mixing/diluting apparatus called central dialysis fluid delivery system. The mixture is then supplied to a bedside console through a tube to carry out hemodialysis via a dialyzer.

While a method for dissolving concentrated fluids A and B and a method that uses central dialysis fluid delivery system have been widely used, in some cases concentrated fluids A and B customized for a patient are set in an individual dialysis apparatus at the bedside to use a dialysis fluid having a different formula for every patient. Although individual dialysis apparatuses are used less often than multipatient dialysis apparatus in Japan, it is very common to use an individual dialysis apparatus overseas, and the mixing ratio of fluid A:fluid B:RO water is sometimes slightly different.

For example, in the case where one unit of central dialysis fluid delivery system is used, a group of patients, e.g., about 30 through 50 patients, are dialyzed with a dialysis fluid having the same composition. The advantage of this method is that producing large amounts of a dialysis fluid having the same composition lessens the labor of medical staff. However, the biocompatibility of the dialysis fluid to individual patients is ignored, and a dialysis fluid that has a composition thought to be mostly compatible to all patients is used.

On the other hand, use of an individual dialysis system has an advantage of allowing selection of a dialysis fluid that has a different composition suitable for every patient, but it is necessary to prepare concentrated fluids A and B for every patient, i.e., for every individual dialysis apparatus, and to control the concentration of the dialysis fluid in the individual dialysis apparatus, and thus the burden of medical staff is significant.

Regarding the current situation of dialysis fluids, a brief discussion of conventional art will now be presented below, including cases in Europe and America.

JP H6-245995A (hereafter referred to as "Patent Literature 2") discloses a method for preparing a dialysis fluid that uses a first or basic concentrate containing sodium chloride and sodium hydrogencarbonate and having a molar ratio of hydrogencarbonate/sodium of 0.3 or less, and a second or individual concentrate containing compositions individually selected according to the physiological requirements to supply the remaining amounts of solutes necessary in the dialysis fluid. The basic concentrate contains 80 to 95% of the total sodium chloride of the final dialysis fluid and serves as a dialysis fluid base, and the individual concentrate containing the remaining 5 to 20% of sodium chloride, potassium, calcium, magnesium, a pH adjuster, and the like is added to the basic concentrate to give the final dialysis fluid. The advantage of this dialysis fluid preparation method is as follows. A basic dialysis fluid is prepared in a central supply unit from the first or basic concentrate, and while causing the basic dialysis fluid to loop-circulate at the bedside of a patient, the second or individual concentrate is supplied before the dialysis fluid reaches a dialyzer, thereby making it possible to select the individual concentrate so as to attain a dialysis fluid composition that is optimum for every patient. Therefore, the method of Patent Literature 2 makes it possible to select potassium, calcium, magnesium, glucose, and the like according to the patient while maintaining the bicarbonate ion concentration in the dialysis fluid at a constant level.

JP Pat. No. 3586767 (hereafter referred to as "Patent Literature 3") discloses a method for preparing a dialysis fluid that uses a dialysis agent composed of an agent A containing sodium chloride, an agent B composed of sodium bicarbonate, and an agent C containing a calcium salt and a magnesium salt, and that includes continuously dissolving the sodium chloride-containing agent A to a constant concentration in a fluid C in which the agent C is dissolved to a specific concentration and mixing this solution with an agent B solution. The dialysis fluid preparation method described in Patent Literature 3 is mainly intended for individual dialysis apparatus, but is silent as to control of the concentrations of components in the dialysis fluid except for setting the components at predetermined constant concentrations.

Moreover, JP Pat. No. 4235555 (hereafter referred to as "Patent Literature 4") discloses a method for priming an extracorporeal circuit using a dialysis apparatus that includes a dialysis fluid control system having a supply source of water and separate supply sources of a bicarbonate concentrate and a sodium chloride concentrate, wherein acid and other electrolyte solutions are added in-line to a sodium chloride solution to give a dialysis fluid A, a fluid B in which a bicarbonate concentrate is dissolved is added in-line to the dialysis fluid A, and the mixture is supplied as a dialyzing fluid to a dialyzer by exchange with a priming fluid. However, Patent Literature 4 also does not describe control of the concentrations of components in the dialysis fluid except for setting the components at predetermined constant concentrations.

JP 2005-198943A (hereafter referred to as "Patent Literature 5") discloses a correction liquid containing potassium chloride, calcium chloride, magnesium chloride, glucose, and the like for a bicarbonate dialysis fluid created by mixing/dilution together with sodium chloride and sodium bicarbonate. Patent Literature 5 does not appear to describe more than obtaining a dialysis fluid having a predetermined constant composition.

As described above, irrespective of multipatient dialysis systems and individual dialysis systems, a dialysis fluid having a constant composition is commonly used, but attempts have been made to select concentrations of calcium, magnesium, potassium, glucose, and the like according to the disease state of an individual.

Meanwhile, as a dialysis fluid to suitably ameliorate metabolic acidosis tailored to individual dialysis patients, a Bifil dialysate has been commercially available. This is composed of a Bifil dialysate, which does not contain an alkaline agent, and a sodium hydrogencarbonate (sodium bicarbonate) replenisher fluid exclusively used for the Bifil dialysate. Dialysis is carried out with the Bifil dialysis fluid, and at the same time the sodium hydrogencarbonate replenisher fluid is continuously introduced into the post-dialyzer blood circuit to ameliorate metabolic acidosis. Use of Bifil is a highly suitable method for ameliorating metabolic acidosis, but because excessively administered sodium hydrogencarbonate easily results in alkalosis, a strict acid-base equilibrium management may be required in one embodiment. In addition to a dialysis operation, an operation to directly inject a replenisher fluid or the like into the blood can easily result in a medical accident, and in fact, a strict warning about medical accidents resulting from use of the Bifil dialysate and sodium hydrogencarbonate replenisher fluid alone is given.

CITATION LIST

Patent Literature

Patent Literature 1: JP H4-75017B
Patent Literature 2: JP H6-245995A
Patent Literature 3: JP Pat. No. 3586767
Patent Literature 4: JP Pat. No. 4235555
Patent Literature 5: JP 2005-198943A

SUMMARY

Technical Problem

As described above, use of Bifil with which sodium hydrogencarbonate is directly injected into the blood after dialysis is among the only blood purification methods that can ameliorate metabolic acidosis of an individual patient, and there is not such a blood purification method using ordinary dialysate and hemodialysis.

In the DOPPS survey in 2004, the mortality and hospitalization risk of dialysis patients were extensively investigated based on the nutrition evaluation and the like for the first time, showing that the optimum blood bicarbonate level before dialysis is 20 to 22 mEq/l, and the risk increases when the blood bicarbonate level is 17 mEq/l or less and 27 mEq/l or greater.

However, the blood bicarbonate level greatly varies according to the nutritional state of a patient, and therefore, it is not necessarily possible to cover the amount of bicarbonate required in all patients with a dialysis fluid having a uniform composition that is regarded as being mostly suitable. Moreover, with currently commercially available dialysates, the average pre-dialysis blood bicarbonate level is mostly within the range of about 19 to 22 mEq/l, but it is well known from examining each patient that there are a large number of cases that do not fall within this range, and so far management of acidosis in a patient, except for control of the average level, has been overlooked. Also, the greater the food intake, the more likely to result in metabolic acidosis, but because that makes the nutritional state of a patient favorable, i.e., close to being healthy, the amount of bicarbonate administered should be comprehensively determined based not only on the disease state of a patient but also the physiological state. Also, because it has been clear that amelioration of metabolic acidosis is an effective means against protein metabolism and dialytic skeletal disorders, it is considered important to suitably control the blood bicarbonate level.

As described above, despite the fact that the importance of controlling the blood bicarbonate level is becoming clear and it is natural that the amount of bicarbonate required for every patient is different, at present a dialysis fluid having a fixed concentration (for example, 25 mEq/l to 30 mEq/l) that is considered to be mostly suitable is uniformly administered, and in some cases it is not possible with such a dialysis fluid to obtain a satisfactory amelioration effect on metabolic acidosis depending on the patient.

Heretofore, the idea of flexibly adjusting the bicarbonate ion concentration in a dialysis fluid so as to suit the disease state of every dialysis patient is absent, and as with the aforementioned Bifil, the bicarbonate ion concentration is adjusted so as to suit the disease state of a dialysis patient merely by using a sodium hydrogencarbonate replenisher fluid that is separate from a dialysis fluid. The ability to flexibly change the bicarbonate ion concentration in a dialysis fluid during dialysis will contribute also to development of a medical technology that makes it possible to more safely and more effectively ameliorate metabolic acidosis. However, based on applicant's knowledge, such an dialysate or dialysis fluid preparation apparatus that can flexibly change the bicarbonate concentration is not known, or no such idea has ever existed.

Accordingly, an object of an embodiment of the present invention is to provide a technology for preparing a dialysis fluid that is capable of flexibly changing the bicarbonate ion concentration even during dialysis according to the disease state or the physiological condition of a patient and maintaining the concentrations of trace metal ions such as potassium ions, calcium ions, and magnesium ions at constant levels.

Solution to Problem

Having conducted diligent research to solve the foregoing problems, the inventors found that, in connection with a three-component dialysate composed of an agent S containing a sodium chloride, an agent B containing a sodium bicarbonate, and an agent A containing electrolyte components other than sodium chloride and sodium bicarbonate, suitably adjusting the amount of the agent B during dialysis fluid preparation makes it possible to maintain the concentrations of trace metal ions such as potassium ions, calcium ions, and magnesium ions in a dialysis fluid at constant levels and flexibly change the bicarbonate ion concentration and control the pH so as to be within an optimum range. Moreover, the inventors also found that, in the three-component dialysate, adjusting the ratio between the amount of the agent S and the amount of the agent B when the dialysate is used makes it possible to maintain the sodium ion concentration at a constant level or flexibly change the sodium ion concentration. Based on these findings, the inventors conducted further research and accomplished various embodiments of the present invention.

That is, in various embodiments, the present invention provides a dialysis fluid preparation apparatus, a dialysis fluid preparation method, and a three-component dialysate as follows:

1. A dialysis fluid preparation apparatus comprising:
   an agent S container that accommodates an agent S containing sodium chloride and has an outlet,
   an agent B container that accommodates an agent B containing sodium bicarbonate and has an outlet,
   an agent A container that accommodates an agent A containing electrolyte components other than sodium chloride and sodium bicarbonate and has an outlet,
   a mixing part in which the agent S discharged from the agent S container, the agent B discharged from the agent B container, and the agent A discharged from the agent A container are mixed to give a dialysis fluid,
   an input part that receives an input of dialysis fluid data containing bicarbonate concentration information that specifies a bicarbonate ion concentration in the dialysis fluid, and
   a control part that controls at least an amount of the agent B supplied to the mixing part based on the dialysis fluid data so as to change the bicarbonate ion concentration in the dialysis fluid,
   the control part controlling the amount of the agent B supplied to the mixing part based on the bicarbonate concentration information, and controlling at least one of the amount of the agent S and the amount of the agent A supplied to the mixing part such that the sodium ion concentration in the dialysis fluid is at a constant level.

2. A dialysis fluid preparation apparatus comprising:
   an agent S container that accommodates an agent S containing sodium chloride and has an outlet,
   an agent B container that accommodates an agent B containing sodium bicarbonate and has an outlet,
   an agent A container that accommodates an agent A containing electrolyte components other than sodium chloride and sodium bicarbonate and has an outlet,
   a mixing part in which the agent S discharged from the agent S container, the agent B discharged from the agent B container, and the agent A discharged from the agent A container are mixed to give a dialysis fluid,
   an input part that receives an input of dialysis fluid data containing bicarbonate concentration information that specifies a bicarbonate ion concentration in the dialysis fluid, and
   a control part that controls at least an amount of the agent B supplied to the mixing part based on the dialysis fluid data so as to change the bicarbonate ion concentration in the dialysis fluid,
   the control part controlling amounts of the agent S and the agent B supplied to the mixing part so as to change the bicarbonate ion concentration and at the same time the sodium ion concentration during dialysis according to a disease state of a patient.

3. The dialysis fluid preparation apparatus according to item 1 or 2, wherein
   a supply of water to the agent S container and the agent B container that accommodate the agent S in a solid form and the agent B in a solid form, respectively, allows the agent S in a liquid form that has a saturated sodium chloride concentration and the agent B in a liquid form that has a saturated sodium bicarbonate concentration to be discharged.

4. The dialysis fluid preparation apparatus according to any of items 1 to 3,
   wherein the agent S discharged from the agent S container is liquid, a liquid agent S supply line that supplies the liquid agent S to the agent B container is further provided, and an S-B mixture of the agent S and the agent B is discharged from the agent B container.

5. The dialysis fluid preparation apparatus according to item 1 or 2, further comprising a dissolution tank in which the agent S in a solid form and the agent B in a solid form discharged from the agent S container and the agent B container, respectively, are dissolved and accommodated and that has an outlet,
   an S-B mixture of the dissolved agent S and agent B being discharged from the dissolution tank and supplied to the mixing part.

6. The dialysis fluid preparation apparatus according to any of items 1 to 5, wherein
   the mixing part is provided with a measuring part that measures an electric conductivity of the dialysis fluid.

7. The dialysis fluid preparation apparatus according to any of items 1 to 6, wherein
   the bicarbonate concentration information is specified for each patient according to a disease state of the patient.

8. The dialysis fluid preparation apparatus according to any of items 1 to 7, further comprising a storage tank that stores pharmaceutical ingredients discharged from at least two of the agent S container, the agent B container, and the agent A container before the pharmaceutical ingredients are supplied to the mixing part,
the control part controlling at least one of an amount of the pharmaceutical ingredients discharged from the storage tank to the mixing part and an amount of the pharmaceutical ingredients flowing into the storage tank.

9. A dialysate having a variable bicarbonate ion concentration,
the dialysate being a three-component dialysate for preparing a dialysis fluid and comprising:
an agent S containing sodium chloride,
an agent B containing sodium bicarbonate, and
an agent A containing electrolyte components other than sodium chloride and sodium bicarbonate,
the dialysate being used such that a ratio between amounts of the agent S and the agent B is adjusted during dialysis according to a disease state of a patient so as to change a bicarbonate ion concentration and to maintain a sodium ion concentration at a constant level or change the sodium ion concentration in the dialysis fluid.

10. The dialysate according to item 9, used so as to change the bicarbonate ion concentration and maintain the sodium ion concentration at a constant level during dialysis according to a disease state of a patient.

11. The dialysate according to item 9, used so as to change the bicarbonate ion concentration and at the same time change the sodium ion concentration during dialysis according to a disease state of a patient.

12. The dialysate according to any of items 9 to 11, used such that the bicarbonate ion concentration in the dialysis fluid is within a range of 20 to 40 mEq/l.

13. The dialysate according to any of items 9 to 12, used such that the bicarbonate ion concentration in the dialysis fluid is within a range of 25 to 35 mEq/l.

14. The dialysate according to any of items 9 to 13, wherein the agent S is solid.

15. The dialysate according to any of items 9 to 14, wherein the agent B is solid.

16. The dialysate according to any of items 9 to 15, wherein the agent A contains neither acetic acid nor a salt thereof.

17. A method for operating a dialysis fluid preparation apparatus including an agent S container that accommodates an agent S containing sodium chloride and has an outlet, an agent B container that accommodates an agent B containing sodium bicarbonate and has an outlet, an agent A container that accommodates an agent A containing electrolyte components other than sodium chloride and sodium bicarbonate and has an outlet, a mixing part in which the agent S discharged from the agent S container, the agent B discharged from the agent B container, and the agent A discharged from the agent A container are mixed to give a dialysis fluid, an input part that receives an input of dialysis fluid data containing bicarbonate concentration information that specifies a bicarbonate ion concentration in the dialysis fluid, and a control part that controls at least an amount of the agent B supplied to the mixing part based on the dialysis fluid data so as to change the bicarbonate ion concentration in the dialysis fluid, the control part operates such that a ratio between amounts of the agent S and the agent B is adjusted so as to change a bicarbonate ion concentration and to maintain a sodium ion concentration at a constant level or change the sodium ion concentration in the dialysis fluid.

18. The method for operating a dialysis fluid preparation apparatus according to item 17, wherein the control part operates such that, according to a disease state of a patient, the bicarbonate ion concentration is changed and the sodium ion concentration is maintained at a constant level during dialysis.

19. The method for operating a dialysis fluid preparation apparatus according to item 17 or 18, wherein the control part operates so as to mix the agent S with the agent B to give an S-B mixture containing sodium chloride and sodium bicarbonate, and mix the S-B mixture with the agent A.

20. The method for operating a dialysis fluid preparation apparatus according to any of items 17 to 19, wherein the control part operates so as to bring the agent S in an aqueous solution form into contact with the agent B in a solid form to give a S-B mixture in a liquid form in which sodium chloride and sodium bicarbonate are dissolved, and mix the liquid S-B mixture with the agent A.

21. The method for operating a dialysis fluid preparation apparatus according to item 20, wherein the agent S in an aqueous solution form has a sodium chloride concentration of 8 to 14 g/100 ml.

22. The method for operating a dialysis fluid preparation apparatus according to item 17, 19, or 20, wherein the control part operates so as to change the bicarbonate ion concentration and at the same time the sodium ion concentration during dialysis according to a disease state of a patient.

23. A dialysis system comprising a dialysis fluid preparation apparatus of item 1 or 2, a dialysate of item 9, and a dialyzer,
an agent S, an agent B, and an agent A contained in the dialysate being accommodated in an agent S container, an agent B container, and an agent A container, respectively, in the dialysis fluid preparation apparatus,
a dialysis fluid prepared in a mixing part in the dialysis fluid preparation apparatus being sent to the dialyzer via a supply line.

24. A preparation method of dialysis fluid comprising a step of mixing an agent S containing sodium chloride, an agent B containing sodium bicarbonate, and an agent A containing electrolyte components other than sodium chloride and sodium bicarbonate,
in the step, a ratio between amounts of the agent S and the agent B is adjusted during dialysis according to a disease state of a patient so as to change a bicarbonate ion concentration and to maintain a sodium ion concentration at a constant level or change the sodium ion concentration in the dialysis fluid.

25. Use of a three-component dialysate comprising:
an agent S containing sodium chloride,
an agent B containing sodium bicarbonate, and
an agent A containing electrolyte components other than sodium chloride and sodium bicarbonate,
for the manufacture of dialysate being used such that a ratio between amounts of the agent S and the agent B is adjusted during dialysis according to a disease state of a patient so as to change a bicarbonate ion concentration and to maintain a sodium ion concentration at a constant level or change the sodium ion concentration in the dialysis fluid.

26. A hemodialysis method comprising subjecting a patient to a hemodialysis using a dialysis fluid prepared with a dialysate, wherein
the dialysate is a three-component dialysate and comprises:
an agent S containing sodium chloride,
an agent B containing sodium bicarbonate, and an agent A containing electrolyte components other than sodium chloride and sodium bicarbonate, and the dialysate is used such that a ratio between amounts of the agent S and the agent B is adjusted during dialysis according to a disease state of the patient so as to change a bicarbonate ion concentration and to maintain a sodium ion concentration at a constant level or change the sodium ion concentration in the dialysis fluid.

Advantageous Effects of Invention

In some embodiments, the optimum bicarbonate ion concentration of a dialysis fluid to attain a target plasma bicarbonate ion concentration level at the end of dialysis varies depending on the patient according to the severity of pre-dialysis metabolic acidosis. Therefore, one can customize the bicarbonate ion concentration of a dialysis fluid for the patient. It cannot be said that suddenly changing from a pre-dialysis metabolic acidosis state to an alkalosis state is necessarily suitable in terms of homeostasis. In this regard, some embodiments of the present invention make it possible to create an upward gradient on the bicarbonate ion concentration of a dialysis fluid during dialysis according to the symptom of a dialysis patient, thus making it possible to cause the plasma bicarbonate ion concentration at the end of dialysis to reach a target level using a program that is most suitable for the symptom of the dialysis patient.

As described above, in one embodiment, the present invention provides a dialysis fluid preparation technology that makes it possible to maintain the concentrations of trace metal ions such as potassium ions, calcium ions, and magnesium ions at constant levels and flexibly change the bicarbonate ion concentration and control the pH so as to be within an optimum range, and thereby it can ameliorate metabolic acidosis in a manner suitable for the disease state of a patient. Therefore, in one embodiment, the present invention can reduce the mortality and hospitalization risk of a dialysis patient, and will be very useful for future dialysis therapy.

Also, one embodiment of the present invention provides a novel type of a dialysis fluid having a variable bicarbonate ion concentration not found in conventional art, and therefore, can contribute also to development of a medical technology for more safely and more effectively ameliorating metabolic acidosis.

DETAILED DESCRIPTION

Figure 1:
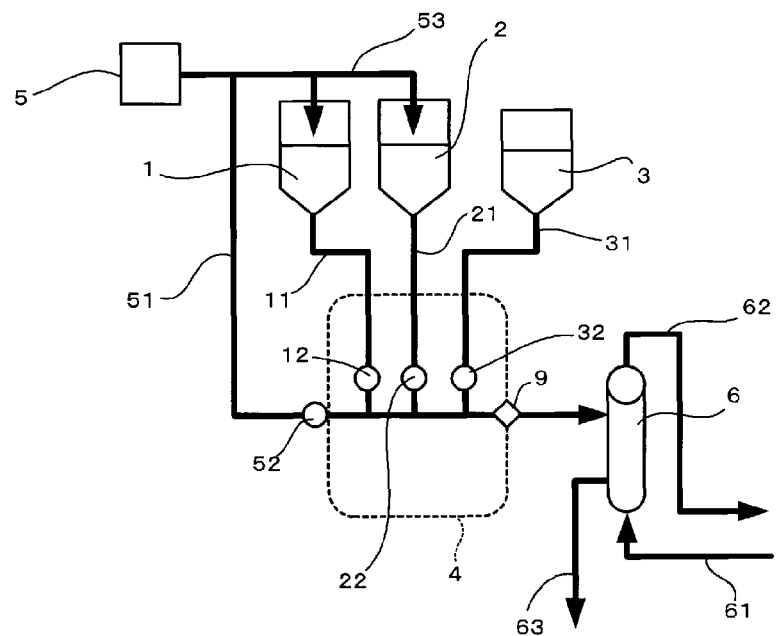
FIG. 1 is a schematic configurational diagram showing the first embodiment of a dialysis fluid preparation apparatus of the present invention.

Herein, the term "dialysis fluid" refers to a fluid supplied to a dialyzer to be used in hemodialysis, and the term "dialysate" refers to a pharmaceutical agent used in dialysis fluid preparation.

1. Dialysate and Preparation of Dialysis Fluid

In one embodiment, the dialysate of the present invention is a three-component dialysate for preparing a dialysis fluid and contains a sodium chloride-containing agent S, a sodium bicarbonate-containing agent B, and an agent A containing electrolyte components other than sodium chloride and sodium bicarbonate, and adjusting the amount of the agent B when the dialysate is used makes it possible to change the bicarbonate ion concentration in a dialysis fluid. Hereinafter, various embodiments of the dialysate of the present invention will now be described in detail.

Agent S

In one embodiment, the agent S contains sodium chloride. In one embodiment, it is desirable that the agent S does not contain any electrolyte component other than sodium chloride, and in one embodiment, it is preferable that the agent S is substantially composed solely of sodium chloride. The agent S may be provided in a solid or aqueous solution form, and the agent S is desirably in a solid form from the viewpoint of easy transportation and storage. Specific examples of the solid form of the agent S include powder, granule, and the like. Herein, the agent S in a solid form may be referred to as a "solid agent S", and the agent S in an aqueous solution form may be referred to as a "liquid agent S".

In some embodiments where the liquid agent S is used, the sodium chloride content of the liquid agent S is, for example, 8 to 32 g/100 ml, preferably 26 to 32 g/100 ml, and more preferably 30 to 31 g/100 ml.

Agent B

In one embodiment, the agent B contains sodium bicarbonate. In one embodiment, it is desirable that the agent B does not contain any electrolyte component other than sodium bicarbonate, and in one embodiment, it is preferable that the agent B is substantially composed solely of sodium bicarbonate. As with the agent S, the agent B also may be provided in a solid or aqueous solution form, and the agent B is desirably in a solid form from the viewpoint of easy transportation and storage. Specific examples of the solid form of the agent B include powder, granule, and the like. Herein, the agent B in a solid form may be referred to as a "solid agent B", and the agent B in an aqueous solution form may be referred to as a "liquid agent B".

In some embodiments where the liquid agent B is used, the sodium bicarbonate content of the liquid agent B may be such that the desired bicarbonate ion concentration is satisfied in the eventually obtained dialysis fluid, and for example, 7 to 12 g/100 ml, preferably 8 to 12 g/100 ml, and more preferably 9 to 11 g/100 ml.

Agent A

In one embodiment, the agent A contains electrolyte components other than sodium chloride and sodium bicarbonate. The electrolyte components contained in the agent A may be those that serve as supply sources of magnesium ions, calcium ions, sodium ions, potassium ions, chloride ions, acetate ions, citrate ions, lactate ions, gluconate ions, succinate ions, malate ions, and the like. Also, the agent A may contain glucose as an optional component.

In one embodiment, it is preferable that those that serve as supply sources of at least magnesium ions and calcium ions as electrolyte components are contained in the agent A, and it is more preferable that those that serve as supply sources of, in particular, magnesium ions, calcium ions, potassium ions, and chloride ions are contained. Moreover, in addition to these, sodium ions and acetate ions may be contained as necessary.

A calcium salt may be a supply source of calcium ions. The calcium salt contained in the agent A is not particularly limited as long as it is acceptable as a component of a dialysis fluid, and examples include calcium chloride, calcium acetate, calcium lactate, calcium citrate, calcium gluconate, calcium succinate, calcium malate, and the like. Among these calcium salts, calcium chloride exhibits great solubility in water, and is thus suitably used as a supply source of calcium ions. The calcium salt used for the agent A may be in a hydrate form. In the agent A, calcium salts may be used singly or used as a combination of two or more.

A magnesium salt may be a supply source of magnesium ions. The magnesium salt contained in the agent A also is not particularly limited as long as it is acceptable as a component of a dialysis fluid, and examples include magnesium chloride, magnesium acetate, magnesium lactate, magnesium citrate, magnesium gluconate, magnesium succinate, magnesium malate, and the like. Among these magnesium salts, magnesium chloride exhibits great solubility in water, and is thus suitably used as a supply source of magnesium ions. The magnesium salt used for the agent A may be in a hydrate form. In the agent A, magnesium salts may be used singly or used as a combination of two or more.

A sodium salt may be a supply source of sodium ions. The sodium salt may be a salt that is used as a pH adjuster and is not particularly limited as long as it is acceptable as a component of a dialysis fluid, and examples include sodium acetate, sodium lactate, sodium citrate, sodium gluconate, sodium succinate, sodium malate, and the like. These sodium salts of organic acids are suitably used because their buffering action improves the pH stability of a dialysis fluid. The sodium salt used for the agent A may be in a hydrate form. In the agent A, sodium salts may be used singly or used as a combination of two or more.

A potassium salt may be a supply source of potassium ions. The potassium salt contained in the agent A also is not particularly limited as long as it is acceptable as a component of a dialysis fluid, and examples include potassium chloride, potassium acetate, potassium lactate, potassium citrate, potassium gluconate, potassium succinate, potassium malate, and the like. Among these potassium salts, potassium chloride exhibits great solubility in water, and is thus suitably used as a supply source of potassium ions. The potassium salt used for the agent A may be in a hydrate form. In the agent A, potassium salts may be used singly or used as a combination of two or more.

Acetic acid and/or a acetate may be a supply source of acetate ions. The acetate may be a salt that is used as a pH adjuster and is not particularly limited as long as it is acceptable as a component of a dialysis fluid, and examples include calcium acetate, magnesium acetate, sodium acetate, potassium acetate, and the like. The acetate used for the agent A may be in a hydrate form. In the agent A, acetic acid and/or acetate may be used singly or used as a combination of two or more.

A chloride salt may be a supply source of chloride ions. The chloride salt also is not particularly limited as long as it is acceptable as a component of a dialysis fluid, and examples include calcium chloride, magnesium chloride, potassium chloride, and the like. The chloride salt used for the agent A may be in a hydrate form. In the agent A, chloride salts may be used singly or used as a combination of two or more. Also, it is also possible to use hydrochloric acid, which is used as a pH adjuster, as a supply source of chloride ions.

The kind and combination of electrolytes contained in various embodiments of the agent A are suitably determined according to the kind of ions to be contained in the eventually prepared dialysis fluid. For example, at least one, preferably two or more, and more preferably three or more of magnesium salts, calcium salts, sodium salts, potassium salts, and acetates may be used as electrolyte components to be contained in the agent A. A suitable specific example of electrolyte components contained in the agent A may be a combination of magnesium chloride, calcium chloride, and potassium chloride.

In one embodiment, one form of a dialysis fluid prepared from the dialysate of the present invention may be an acetate-free dialysis fluid. In one embodiment, in the case of an acetate-free dialysis fluid, electrolytes to be contained in the agent A are selected such that no acetate ion supply source (i.e., neither acetic acid nor salts thereof) is contained.

The amounts of electrolyte components contained in the agent A are suitably set according to the concentrations of ions attained in the eventually prepared dialysis fluid. Specifically, the amounts of electrolyte components contained in the agent A are suitably set in consideration of the amounts of electrolyte components contained in the agent S and the agent B such that the eventually prepared dialysis fluid satisfies the ion concentrations shown in Table 1 below.

TABLE 1

| | Concentration in dialysis fluid |
|---|---|
| Sodium ion | 120 to 150 mEq/l, preferably 135 to 145 mEq/l |
| Potassium ion | 0.5 to 3 mEq/l, preferably 1.5 to 2.5 mEq/l |
| Calcium ion | 1.5 to 4.5 mEq/l, preferably 2.5 to 3.5 mEq/l |
| Magnesium ion | 0 to 2.0 mEq/l, preferably 0.5 to 1.5 mEq/l |
| Acetate ion | 0 to 12 mEq/l, preferably 0 to 10 mEq/l |
| Citrate ion | 0 to 18 mEq/l |
| Chloride ion | 90 to 135 mEq/l, preferably 100 to 120 mEq/l |
| Lactate ion | 0 to 10 mEq/l |
| Malate ion | 0 to 10 mEq/l |
| Gluconate ion | 0 to 10 mEq/l |
| Succinate ion | 0 to 10 mEq/l |

Note that the sodium ion concentration shown in Table 1 above includes sodium ions derived from the agent S and the agent B, and the amount of sodium salt contained in the agent A is determined in consideration of the amount of sodium ion supplied from the agent S and the agent B. Also, the chloride ion concentration shown in Table 1 above also includes chloride ions derived from the agent S, and the amount of chloride salt contained in the agent A is determined in consideration of the amount of chloride ion supplied from the agent S.

For example, in some embodiments, in the case where magnesium chloride, calcium chloride, sodium acetate, and potassium chloride are used as electrolytes to be contained in the agent A, in order to satisfy the ranges of the concentrations of ions contained in a dialysis fluid shown in Table 1, the ratio of electrolytes in the agent A may be set such that calcium chloride is 0.75 to 2.25 mol and preferably 1.25 to 1.75 mol, acetic acid and sodium acetate are 0 to 12 mol and preferably 0 to 10 mol, and potassium chloride is 0.5 to 3 mol and preferably 1.5 to 2.5 mol relative to 0.5 mol of magnesium chloride.

Also, the agent A may contain glucose to maintain the blood sugar level of a patient in addition to the foregoing electrolytes. The amount of glucose in the agent A is suitably set according to the glucose concentration to be attained in the eventually prepared dialysis fluid. Specifically, the amount of glucose in the agent A is suitably set such that the glucose concentration in the eventually prepared dialysis fluid is 0 to 2.5 g/l and preferably 1.0 to 1.5 g/l.

Moreover, the agent A may contain an acid to adjust the pH of the eventually prepared dialysis fluid. Examples of the acid contained in the agent A include liquid acids such as acetic acid, hydrochloric acid, lactic acid, and gluconic acid; solid acids such as citric acid, succinic acid, fumaric acid, malic acid, and glucono delta-lactone; and the like. The amount of acid contained in the agent A is suitably set according to the pH to be exhibited by the eventually prepared dialysis fluid, the kinds of acid, and the like. Specifically, the amount of acid contained in the agent A is suitably set such that the pH of the eventually prepared dialysis fluid is 7.2 to 7.6 and preferably 7.2 to 7.5.

The agent A may be provided in a solid, paste, or aqueous solution form. Examples of the solid form of the agent A include, although it is not particularly limited to, powder, granule, and the like. When the agent A in a solid or paste form is used, the agent A is dissolved in a specific amount of water that has been introduced into a container, and then the agent A is used as an aqueous solution. Herein, the agent A in a solid form may be referred to as a "solid agent A", and the agent A in an aqueous solution form may be referred to as a "liquid agent A".

In the case where the liquid agent A is used, the amounts of the respective components contained in the liquid agent A are not particularly limited, and for example, the components may be concentrated about 35 to 500 fold and preferably 200 to 400 fold relative to the concentrations of the respective components in the eventually prepared dialysis fluid.

2. Preparation of Dialysis Fluid Using Agent S, Agent B, and Agent A

In one embodiment, a dialysis fluid is prepared through the step of adding/mixing the desired amounts of the above-described agent S, agent B and agent A as well as water if necessary.

In one embodiment, in the preparation of a dialysis fluid using the dialysate of the present invention, water is added as necessary in order to adjust the concentrations of the components of the eventually obtained dialysis fluid. Water used when preparing a dialysis fluid from the dialysate of the present invention may be purified to such an extent that it is pharmacologically acceptable. Specifically, water may satisfy the quality of purified water defined by The Japanese Pharmacopoeia. For example, water for use in the preparation of a dialysis fluid may be prepared by subjecting tap water or ground water to activated carbon treatment, softening treatment, or the like for pretreatment, and then subjecting the pretreated water to purification treatment by reverse osmosis membrane filtration, distillation, ultrafiltration, or the like. Also, water used when preparing a dialysis fluid may be commercially available purified water or distilled water.

Control of Concentrations of Dialysis Fluid Components

In one embodiment, when adding/mixing the agent S, the agent B, and the agent A as well as water if necessary during the preparation of a dialysis fluid, maintaining the ratio of the amount of the agent A to the total amount of the eventually obtained dialysis fluid at a constant level and adjusting the amount of the agent B make it possible to maintain the concentrations of ions such as potassium ions, calcium ions, and magnesium ions in the dialysis fluid at constant levels and flexibly change the bicarbonate ion concentration and control the pH so as to be within an optimum range. Also, adjusting the ratio between the amounts of the agent S and the agent B makes it possible to flexibly change the bicarbonate ion concentration in the dialysis fluid and maintain at a constant level or change the sodium ion concentration therein.

An embodiment of a method for controlling the concentrations of dialysis fluid components will now be described in detail below. Specifically, first, the concentrations of the components of the eventually obtained dialysis fluid are set. At this time, the concentrations of the components derived from the agent A other than sodium ions and chloride ions (hereinafter sometimes referred to as "agent A components (excluding Na and Cl)" are set so as to be always at constant levels in the eventually obtained dialysis fluid.

Specifically, the bicarbonate ion concentration in the dialysis fluid may be set so as to be at a constant level or change within the range of 20 to 40 mEq/l and preferably 25 to 35 mEq/l during dialysis. The bicarbonate ion concentration in the dialysis fluid can be set according to the disease state of a patient and, for example, may be set so as to be at a constant level or may be set so as to change within the aforementioned range during dialysis. The disease state of a patient as referred to herein includes, for example, the degree of metabolic acidosis, the nutritional status, and the condition during dialysis of a patient.

The bicarbonate ion concentration in the dialysis fluid is changed, for example, in the following manners (1) to (8):

(1) Lower the bicarbonate ion concentration from the beginning to the end of dialysis treatment;

(2) Raise the bicarbonate ion concentration from the beginning to the end of dialysis treatment;

(3) Lower the bicarbonate ion concentration from the beginning to halfway through dialysis treatment, and then maintain the bicarbonate ion concentration at a constant level to the end;

(4) Raise the bicarbonate ion concentration from the beginning to halfway through dialysis treatment, and then maintain the bicarbonate ion concentration at a constant level to the end;

(5) Maintain the bicarbonate ion concentration at a constant level from the beginning to halfway through dialysis treatment, and then raise the bicarbonate ion concentration level to the end;

(6) Maintain the bicarbonate ion concentration at a constant level from the beginning to halfway through dialysis treatment, and then lower the bicarbonate ion concentration to the end;

(7) Lower the bicarbonate ion concentration from the beginning to halfway through dialysis treatment, and then raise the bicarbonate ion concentration to the end; and (8) Raise the bicarbonate ion concentration from the beginning to halfway through dialysis treatment, and then lower the bicarbonate ion concentration to the end.

These manners of changing the bicarbonate ion concentration are merely illustrative, and needless to say, the bicarbonate ion concentration may be continuously, stepwise, intermittently, or repetitively changed during dialysis in a manner different from (1) to (8) above according to the disease state or physiological condition of a patient.

Also, the sodium ion concentration in the dialysis fluid may be set so as to be, for example, 120 to 150 mEq/l and preferably 135 to 145 mEq/l. The sodium ion concentration in the dialysis fluid may be set at a constant level according to the disease state of a patient or the condition thereof during dialysis or set so as to change within the aforementioned range during dialysis.

For example, in one embodiment, it is in some cases difficult to sufficiently drain water from patients who are likely to be overhydrated, such as hypotensive patients and patients suffering diabetes, with the sodium ion concentration (140 mEq/l) of a dialysis fluid that is now widely used. For such patients, a high-sodium dialysis fluid having a sodium concentration of about 145 to 160 mEq/l is sometimes used. High-sodium dialysis raises plasma osmolarity, efficiently draws intracellular water into the blood, and increases the circulating plasma volume, and is thus thought to be useful to prevent a blood-pressure decrease during dialysis, but high-sodium dialysis is problematic in that it increases the body weight due to thirst during an interdialysis period, and therefore, a method that sets the sodium ion concentration at a high level at the beginning of dialysis and lowers the sodium ion concentration in a stepwise manner thereafter, a method that alternately switch between a high sodium concentration and a proper or low sodium concentration at a specific interval, and a like method that makes it possible to change the sodium ion concentration according to the patient and at the same time change the bicarbonate ion concentration are more preferable for patients.

In the case where hemodialysis is carried out on hyponatremia and hypernatremia patients, it is known that it is effective to set the sodium ion concentration in a dialysis fluid according to the symptoms of these patients, and moreover, it is desirable to change the sodium ion concentration in a dialysis fluid during dialysis according to the conditions of the patients. Specifically, in the case of a hyponatremia patient, it is desirable to set the dialysis fluid at a high sodium ion concentration at the beginning of dialysis and gradually lower the sodium ion concentration during dialysis such that the serum sodium ion concentration does not exceed the optimum concentration at the end of dialysis and satisfies a suitable sodium ion concentration at the end of dialysis. Also, in the case of a hypernatremia patient, it is desirable to set the dialysis fluid at a low sodium ion concentration at the beginning of dialysis and gradually raise the sodium ion concentration during dialysis such that the serum sodium ion concentration does not fall below the optimum concentration at the end of dialysis and satisfies a suitable sodium ion concentration at the end of dialysis.

In the case where hemodialysis is carried out on patients suffering from a disdialysis syndrome or patients who wish to suppress weight gain during a dialysis period, it is known that it is effective to set the sodium ion concentration in a dialysis fluid according to the patient type, and it is desirable to change the sodium ion concentration in a dialysis fluid according to the patient type. For example, for disdialysis syndrome patients, it is desirable to set the sodium ion concentration such that a high sodium ion concentration is set at the beginning of dialysis, dialysis at a high sodium ion concentration is maintained for a relatively long period of time, and then the sodium ion concentration is lowered in a stepwise manner.

Moreover, the symptom of a patient in a dialysis introductory period is less stable than that of a patient in a dialysis maintenance period, and it is desirable to set an optimum program according to the symptom of a dialysis patient.

In one embodiment, the ratio of sodium ions to bicarbonate ions in a dialysis fluid may be in a range that satisfies 0.16 to 0.26 mEq of bicarbonate ions per mEq of sodium ions. In the case where the bicarbonate ion concentration is changed and the sodium ion concentration is maintained at a constant level in the dialysis fluid during dialysis, or in the case where the bicarbonate ion concentration and the sodium ion concentration in the dialysis fluid are both changed during dialysis, it is desirable to set a range within which the bicarbonate ion concentration and the sodium ion concentration in the dialysis fluid are allowed to change and that satisfies the aforementioned ratio.

In one embodiment, the concentrations of the A agent components (excluding Na and Cl) in the dialysis fluid may be such that calcium ions are 1.5 to 4.5 mEq/l and preferably 2.5 to 3.5 mEq/l; magnesium ions are 0 to 2.0 mEq/l and preferably 0.5 to 1.5 mEq/l; potassium ions are 0.5 to 3.0 mEq/l and preferably 1.5 to 2.5 mEq/l; acetate ions are 0 to 12 mEq/l and preferably 0 to 10 mEq/l; and glucose is 0 to 2.5 g/l and preferably 1.0 to 1.5 g/l. The concentrations of the agent A components (excluding Na and Cl) in the dialysis fluid are set so as not to change during dialysis but to be at constant levels.

In one embodiment, note that the chloride ion concentration in the dialysis fluid is usually 90 to 135 mEq/l and preferably 100 to 120 mEq/l. Because the chloride ion concentration in the eventually obtained dialysis fluid depends on the amount of chloride ions derived from the agent S and the agent A, the chloride ion concentration is thus not necessarily at a constant level and may change due to the change of the amount of the agent S. Note that the change of the amount of the agent S brought about to adjust the sodium ion concentration does not result in a change of the chloride ion concentration in the dialysis fluid to such an extent that the serum chloride ion concentration is significantly outside the normal range, and thus the performance of the dialysis fluid is not affected.

After the concentrations of the components in the dialysis fluid are set in the above-described manner, the amounts of the agent S, the agent B and the agent A as well as water that is used if necessary are determined.

Specifically, the amount of the agent A is set such that the set concentrations of the agent A components (excluding Na and Cl) (constant levels) in the dialysis fluid are satisfied.

The amount of the agent B is set according to the set concentration of bicarbonate ions (a variable level) in the dialysis fluid. Moreover, the amount of the agent S is set according to the set concentration of sodium ions (a fixed or variable level) in the dialysis fluid in consideration of the amount of sodium ions derive from the agent B and the agent A added.

More specifically, the amounts of the agent S and the agent B are determined as follows. That is, where the sodium ion concentration and the bicarbonate ion concentration in the dialysis fluid are $\alpha$ mEq/l and $\beta$ mEq/l, respectively, and the sodium ions supplied from the agent A account for $\gamma$ mEq/l of the sodium ion concentration $\alpha$ mEq/l, the amounts of the agent S and the agent B required in preparation of the dialysis fluid in a volume of 1 L are as follows:

Amount of agent S=amount that provides sodium ions in an amount corresponding to (α-β-γ) mEq/l Amount of agent B=amount that provides bicarbonate ions in an amount corresponding to β mEq/l That is, changing the amount of the agent B makes it possible to change the bicarbonate ion concentration β mEq/l in the dialysis fluid. Also, regarding the sodium ion concentration α mEq/l in the dialysis fluid, adjusting the amount of the agent S makes it possible to maintain the change of the sodium ion concentration brought about by the change of the bicarbonate ion concentration at a constant level or flexibly set or change it within a high content range exceeding (α+γ) mEq/l.

In one embodiment, the amount of water is set such that the concentrations of the components of the eventually obtained dialysis fluid satisfy specific levels. Specifically, the amount of water is set in consideration of, for example, whether the agent S, the agent B, and the agent A are in a solid or liquid form and how much the water content is if at least one of these is in a liquid form.

That is, in the preparation of a dialysis fluid using the dialysate of the present invention, causing the amount of the agent A to be at a constant level makes it possible to maintain the concentrations of the agent A components (excluding Na and Cl) in the dialysis fluid at constant levels. Also, adjusting the amount of the agent B makes it possible to flexibly change the bicarbonate ion concentration in the dialysis fluid. Moreover, adjusting the amount of the agent S makes it possible to maintain the sodium ion concentration in the dialysis fluid at a constant level or change the sodium ion concentration therein.

As a more specific example, in one embodiment, a case where a liquid agent S containing 31 g/100 ml of sodium chloride, a liquid agent B containing 10 g/100 ml of sodium bicarbonate, and a liquid agent A containing 2.61 g/100 ml of potassium chloride, 3.86 g/100 ml of calcium chloride hydrate, 1.78 g/100 ml of magnesium chloride hydrate, 2.10 g/100 ml of acetic acid, 8.61 g/100 ml of sodium acetate, and 17.50 g/100 ml of glucose will now be presented to describe a method that changes the bicarbonate ion concentration in a dialysis fluid while the sodium ion concentration therein at a constant level.

Adding/mixing the aforementioned liquid agent S, liquid agent B, liquid agent A, and water in a volume ratio of 6.86:8.82:2.00:332.32 gives a dialysis fluid having a bicarbonate ion concentration of 30 mEq/l and a sodium ion concentration of 140 mEq/l. Adding/mixing the aforementioned liquid agent S, liquid agent B, liquid agent A, and water in a volume ratio of 6.53:10.29:2.00:331.18 gives a dialysis fluid having a bicarbonate ion concentration of 35 mEq/l and a sodium ion concentration of 140 mEq/l. That is, adjusting the ratio of the amount of the liquid agent S to the amount of the liquid agent B makes it possible to change the bicarbonate ion concentration without changing the sodium ion concentration or the concentrations of the agent A components (excluding Na and Cl) in a dialysis fluid.

Also, in one embodiment, a case where a liquid agent S containing 31 g/100 ml of sodium chloride, a liquid agent B containing 10 g/100 ml of sodium bicarbonate, and a liquid agent A containing 2.61 g/100 ml of potassium chloride, 3.86 g/100 ml of calcium chloride hydrate, 1.78 g/100 ml of magnesium chloride hydrate, 2.10 g/100 ml of acetic acid, 8.61 g/100 ml of sodium acetate, and 17.50 g/100 ml of glucose will now be presented to describe a method that changes the bicarbonate ion concentration and that changes as desired the sodium ion concentration in a dialysis fluid.

Adding/mixing the aforementioned liquid agent S, liquid agent B, liquid agent A, and water in a volume ratio of 7.52:7.35:2.00:333.13 gives a dialysis fluid having a bicarbonate ion concentration of 25 mEq/l and a sodium ion concentration of 145 mEq/l. Adding/mixing the aforementioned liquid agent S, liquid agent B, liquid agent A, and water in a volume ratio of 6.20:10.29:2.00:331.51 gives a dialysis fluid having a bicarbonate ion concentration of 35 mEq/l and a sodium ion concentration of 135 mEq/l. That is, adjusting the ratio between the amount of the liquid agent S and the amount of the liquid agent B makes it possible to change the bicarbonate ion concentration and the sodium ion concentration without changing the concentrations of the agent A components (excluding Na and Cl) in a dialysis fluid.

Mixing Agent S, Agent B, and Agent A

In the preparation of a dialysis fluid using the dialysate of one embodiment of the present invention, the order of mixing the agent S, the agent B, the agent A, and water that is used as necessary is not particularly limited. Examples include a method in which the agent S, the agent B, the agent A, and water that is used as necessary are added and mixed simultaneously (hereinafter referred to as mixing manner 1); a method in which specific amounts of the agent S, the agent B, and water that is used as necessary are mixed to give an S-B mixture, and then specific amounts of the S-B mixture, the agent A, and water that is used as necessary are mixed (hereinafter referred to as mixing manner 2); a method in which specific amounts of the agent S, the agent A, and water that is used as necessary are mixed to give an S-A mixture, and then specific amounts of the S-A mixture, the agent B, and water that is used as necessary are mixed (hereinafter referred to as mixing manner 3); a method in which specific amounts of the agent B, the agent A, and water that is used as necessary are mixed to give an B-A mixture, and then specific amounts of the B-A mixture, the agent S, and water that is used as necessary are mixed (hereinafter referred to as mixing manner 4); and the like.

Here, in one embodiment, in the case where the agent S is provided in a solid form, the solid agent S may be dissolved in water in advance to form the above-described liquid agent S when preparing a dialysis fluid. Also, in the case where the agent B is provided in a solid form, the solid agent B may be dissolved in water in advance to form the above-described liquid agent B when preparing a dialysis fluid. Moreover, as for the agent A also, in the case where the agent A is provided in a solid or paste form, the solid agent A may be dissolved in water in advance to form the above-described liquid agent A when preparing a dialysis fluid.

In one embodiment, in the mixing manner 2, the preparation of the S-B mixture and the mixing of the S-B mixture and the agent A may be carried out in the same vessel or carried out separately in two different vessels. Also, in the mixing manner 3, the preparation of the S-A mixture and the mixing of the S-A mixture and the agent B may be carried out in the same vessel or carried out separately in two different vessels. Moreover, in the mixing manner 4 also, the preparation of the B-A mixture and the mixing of the B-A mixture and the agent S may be carried out in the same vessel or carried out separately in two different vessels.

In one embodiment, in the mixing manner 2, in the case where the S-B mixture is prepared by bringing a specific concentration of the liquid agent S into contact with an excessive amount of the solid agent B, the sodium ion concentration in the S-B mixture (liquid) is always at a constant level (a saturated concentration), and bicarbonate ions contained in the S-B mixture (liquid) are equimolar to sodium ions that dissolve from the solid agent B. For example, in the case where the liquid agent S containing 13.99 g/100 ml of sodium chloride is brought into contact with an excessive amount of the solid agent B, the resulting S-B mixture (liquid) has a saturated sodium ion concentration and contains 6.7 mEq of sodium ions per mEq of bicarbonate ions. Also, for example, in the case where the liquid agent S containing 8.08 g/100 ml of sodium chloride is brought into contact with an excessive amount of the solid agent B, the resulting S-B mixture (liquid) has a saturated sodium ion concentration and contains 3.35 mEq of sodium ions per mEq of bicarbonate ions.

That is, in one embodiment, in the case where the S-B mixture (liquid) is prepared by bringing the liquid agent S into contact with an excessive amount of the solid agent B, changing the sodium chloride concentration of the liquid agent S to be supplied makes it possible to change the bicarbonate ion concentration in the S-B mixture (liquid) and maintain the sodium ion concentration at a constant level. Therefore, the mixing manner 2 carried out in such a way is preferable for preparing a dialysis fluid in which the sodium ion concentration is maintained at a constant level and the bicarbonate ion concentration is changed. Here, regarding the liquid agent S that is brought into contact with an excessive amount of the solid agent B to change the bicarbonate ion concentration within 20 to 40 mEq/l, it is desirable that the sodium chloride concentration is set at 8 to 14 g/100 ml. Examples of methods for bringing the liquid agent S into contact with an excessive amount of the solid agent B include a method in which the liquid agent S is passed through a column filled with the solid agent B; a method in which the liquid agent S is supplied to a container accommodating an excessive amount of the solid agent B to give the S-B mixture (liquid) in the container, and the S-B mixture (liquid) is removed from the container; and like methods.

3. Dialysis Fluid Preparation Apparatus

Below, embodiments of the dialysis fluid preparation apparatus of the present invention will now be described with reference to the drawings. Here, three embodiments of dialysis fluid preparation apparatuses according to the manners of mixing the dialysate are described.

First Embodiment

Figure 2:
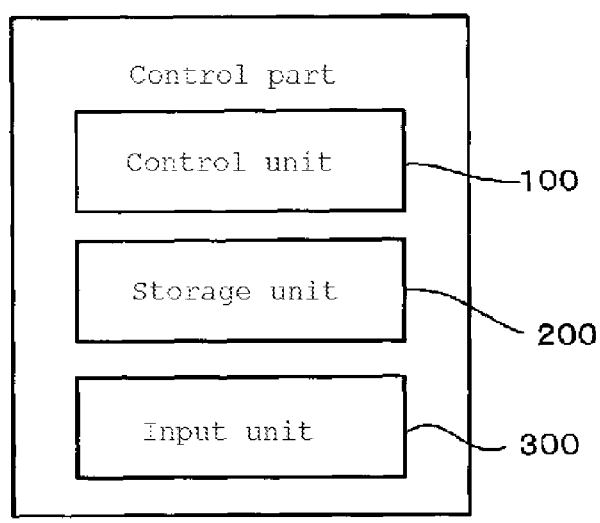
FIG. 2 is a block diagram of a control part used in the dialysis fluid preparation apparatus of FIG. 1.

The dialysis fluid preparation apparatus of the first embodiment will now be described with reference to FIGS. 1 and 2. FIG. 1 is a schematic configurational diagram of the dialysis fluid preparation apparatuses of this embodiment, and FIG. 2 is a block diagram showing the schematic configuration of a control part. As shown in FIG. 1, this apparatus includes an agent S container 1, an agent B container 2, and an agent A container 3 that accommodate the above-described agent S, agent B, and agent A, respectively, and this apparatus also includes a mixing part 4 that mixes pharmaceutical ingredients discharged from the containers 1, 2 and 3, and the control part (not shown) that controls mixing of the pharmaceutical ingredients. The containers 1, 2, and 3 accommodate the solid or liquid agent S, agent B, and agent A, respectively. This apparatus also includes a supply source 5 that supplies water and, between the supply source 5 and the mixing part 4, a main supply line 51 that supplies water. Note that a separate device can be used for the water supply source. A first water pump 52 is attached to the main supply line 51 at the junction with the mixing part 4, thus making it possible to adjust the flow of water into the mixing part 4. A water supply line 53 that supplies water to the agent S container and the agent B container is connected to the middle of the main supply line 51, and thus the solid agent S and the solid agent B accommodated in the agent S container 1 and the agent B container 2, respectively, are dissolved/diluted with water. The rate of water supplied through the water supply line 53 is not particularly limited, and water may be supplied such that a specific amount of water can be always maintained by float switches (not shown) and the like provided for the agent S container 1 and the agent B container 2. The main supply line 51 meets the pharmaceutical ingredients in the mixing part 4 as described below and then is connected to a dialyzer 6. An electric conductivity meter (measuring part) 9 is provided at the outlet of the mixing part 4, and measures the conductivity of the prepared dialysis fluid. The dialyzer 6 includes a blood feed line 61 through which blood from a patient is received, a blood return line 62 thorough which blood is returned to the patient, and a waste fluid line 63 through which a dialyzed waste fluid is discharged. Note that the mixing part 4 may be a mixing chamber, and in such a case, a three-way valve or a circulating pump (not shown) that sends a fluid back to the mixing chamber may be provided downstream of the electric conductivity meter 9, and thus the dilution/mixing state of the pharmaceutical agents can be monitored based on the conductivity while circulating the diluted/mixed fluid, and control in which a fluid is sent to the dialyzer 6 only when a suitable conductivity is satisfied can be performed.

The agent S container 1, the agent B container 2, and the agent A container 3 each have an outlet, and discharge lines 11, 21, and 31 through which discharged solutions travel are connected to the outlets. The discharge lines 11, 21, and 31 are connected to the main supply line 51 that passes through the mixing part 4, and the solutions discharged from the containers 1, 2, and 3 are supplied to the main supply line 51. An agent S pump 12, an agent B pump 22, and an agent A pump 32 disposed in the mixing part 4 are attached to the discharge lines 11, 21, and 31, respectively, and the pumps 12, 22, and 32 adjust the amounts (flow rates) of the pharmaceutical ingredients supplied to the main supply line 51 from the containers 1, 2, and 3. The above-described pumps 12, 22, 32, and 52 are electrically connected to the control part and control the amounts (flow rates) of water and the pharmaceutical ingredients that flow through the main supply line 51 and the discharge lines 11, 21, and 31.

As shown in FIG. 2, the control part is configured with a known general-purpose computer or the like and includes a control unit 100 that is configured with a CPU, a memory, and the like, a storage unit 200 that is configured with a hard disk and the like and stores data and programs, and an input unit (input part) 300 through which an operation of the dialysis fluid preparation apparatus is performed or data is input. The storage unit 200 stores various types of data, and in this embodiment, dialysis fluid data about a dialysis fluid composition set for every patient and a dialysis fluid adjustment program are installed thereon. The dialysis fluid data includes a method for preparing a dialysis fluid in accordance with the disease state of a patient. Also, the input unit 300 may be configured such that dialysis fluid data is directly input using a mouse, keyboard and the like or a touch panel in reference to a display device such as a monitor, or such that data is input from a variety of recording media (such as CDs (registered trademark) and flash memories) in which dialysis fluid data is stored. Alternatively, the input unit 300 can be configured such that dialysis fluid data can be input from an external device via a network (such as a LAN or internet).

The data is usually made based on the judgment of a physician according to the disease state of a dialysis patient, but it is also possible to measure the pre-dialysis blood bicarbonate level of a patient as necessary and, in consideration of the living conditions or nutritional status of the patient, change the sodium level or the bicarbonate level of a dialysis fluid during dialysis. A specific preparation method is as described above. Dialysis fluid data includes, for example, the flow rates of water, the liquid agent S, the liquid agent B, and the liquid agent A to administer a dialysis fluid set at a bicarbonate ion concentration (bicarbonate ion concentration information) suitable for the symptom of a patient (set such that the bicarbonate ion concentration is changed over time as necessary). Therefore, once dialysis fluid data is input into the control part, the control part controls the drives of the pumps 12, 22, 32, and 52 based on the aforementioned adjustment program in reference to the dialysis fluid data. Note that the dialysis fluid data and the adjustment program can be variously configured, and for example, can be configured such that dialysis fluid data includes only the amount of change over time of the bicarbonate ion concentration suitable for the condition of a patient (bicarbonate ion concentration information), and once the data is input through the input unit 300, the adjustment program automatically calculates the flow rates of water, the liquid agent S, the liquid agent B, and the liquid agent A so as to control the drives of the pumps 12, 22, 32, and 52. Also, the dialysis fluid data and the adjustment program may be configured such that once the initial level of the bicarbonate ion concentration is input into the control part, the amounts of change over time of water, the liquid agent S, the liquid agent B, and the liquid agent A are automatically calculated based on the data stored in advance.

Next, actions of the dialysis fluid preparation apparatus configured as described above will now be described. First, in the control part, an adjustment program is started, and dialysis fluid data is input. Thereby, the control part retrieves the flow rates over time of water, the liquid agent S, the liquid agent B, and the liquid agent A, and drives the apparatus as follows. At this time, specific amounts of the solid agent S and the solid agent B are accommodated in advance in the agent S container 1 and the agent B container 2, respectively, and the liquid agent A prepared so as to have a specific concentration is accommodated in the agent A container 3. Thereby, the liquid agent A prepared in advance can be discharged from the agent A container 3. Next, water at a specific temperature is supplied to the agent S container 1 and the agent B container 2 through the water supply line 53 from the supply source 5. Thereby, the solid agent S and the solid agent B dissolve, and thus specific concentrations of the liquid agent S and the liquid agent B are formed and can be discharged through the discharge lines 11 and 21, respectively. In addition to this configuration, it is possible to provide solid agent introduction parts for the agent S container 1 and agent B container 2 such that large amounts of the solid agent S and solid agent B can be introduced into the containers 1 and 2, respectively. Thereby, water is supplied to excessive amounts of the solid agent S and the solid agent B, and thus the liquid agent S that always contains a constant concentration (saturated concentration) of sodium chloride and the liquid agent B that always contains a constant concentration (saturated concentration) of sodium bicarbonate can be continuously discharged without interruption. Note that, in place of such introduction parts, columns accommodating solid agents can be also disposed in the respective containers 1 and 2.

In this state, the control part controls the four pumps 12, 22, 32, and 52 and adjusts the flow rates of water, the liquid agent S, the liquid agent B, and the liquid agent A introduced into the mixing part 4 so as to attain the concentrations as set. It is also possible that the control part controls the pumps so as to attain the desired concentrations based on the concentration of a dialysis fluid measured by the electric conductivity meter 9. Note that details of mixing are as described in the section titled "2. Preparation of dialysis fluid using agent S, agent B, and agent A", and the control part controls the pumps according to the settings. Thereby, the liquid agent S, the liquid agent B, and the liquid agent A are supplied to water flowing through the main supply line 51, and a dialysis fluid is prepared. The dialysis fluid prepared in this way is supplied to the dialyzer 6, and dialysis is carried out. In the process above, because, for example, the bicarbonate ion concentration in the dialysis fluid can be changed over time, the control part can control the drive of the agent B pump 22 and can change the flow rate of the liquid agent B supplied to water. Accordingly, the flow rates of other pumps are also adjusted such that the sodium concentration in the dialysis fluid is at a constant level. It is thus possible to supply a dialysis fluid in which the bicarbonate ion concentration changes and the sodium ion concentration is at a constant level or changes according to the symptom of a patient.

Second Embodiment

Figure 3:
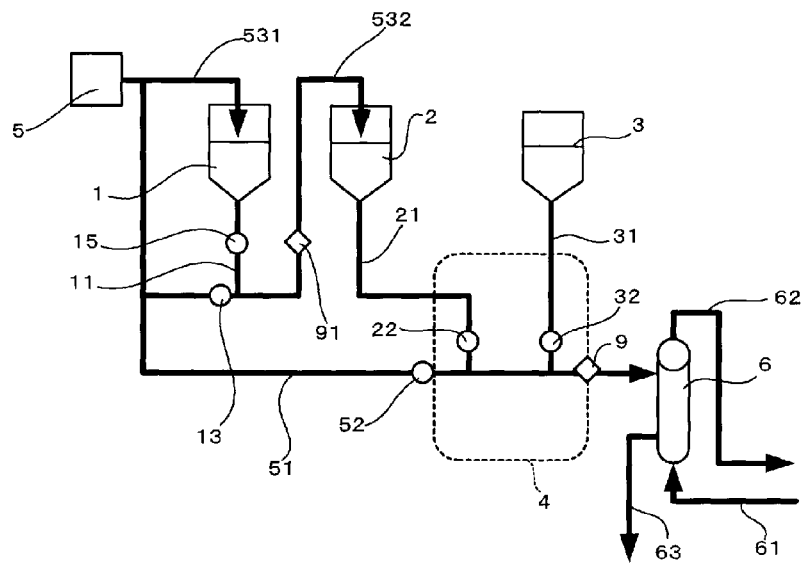
FIG. 3 is a schematic configurational diagram showing the second embodiment of a dialysis fluid preparation apparatus of the present invention.

Next, the second embodiment of the dialysis fluid preparation apparatus of the present invention will now be described in reference to FIG. 3. FIG. 3 is a schematic configurational diagram showing the second embodiment of the dialysis fluid preparation apparatus. The second embodiment commonly shares many features with the first embodiment, such as the agent S container, the agent B container, and the agent A container, and therefore, the same components as in the first embodiment are given the same numerical references unless specified otherwise, and different features are mainly described in the following description. As shown in FIG. 3, in this apparatus, the supply line to supply water from the main supply line 51 branches. That is, a first water supply line 531 that supplies water to the agent S container 1 and a second water supply line (liquid agent S supply line) 532 that supplies water to the agent B container 2 are provided. The discharge line 11 extending from the outlet of the agent S container 1 is connected to the middle of the second water supply line 532, and an agent S discharge pump 15 is provided on the discharge line 11. Also, on the second water supply line 532, an agent S branch pump 13 is provided upstream of the place where the discharge line 11 is connected. Moreover, on the second water supply line 532, an electric conductivity meter 91 is attached downstream of the part where the discharge line 11 is connected, and the concentration of the liquid agent S flowing therethrough is measured. The discharge lines 21 and 31 connected to the outlets of the agent B container 2 and the agent A container 3, respectively, are connected to the main supply line 51 in the mixing part 4 as in the first embodiment. Also, the agent S container 1 and the agent B container 2 are each provided with a solid agent introduction part and configured so as to be capable of introducing large amounts of the solid agent S and the solid agent B to the containers 1 and 2, respectively. In place of such introduction parts, columns accommodating solid agents can be also disposed in the respective containers 1 and 2. Other configurations are the same as the first embodiment.

Next, actions of the dialysis fluid preparation apparatus will now be described. First, the control part is operated to supply water to the agent S container 1 via the first water supply line 531. Thereby, water is supplied to an excessive amount of the solid agent S, and it is thus possible to discharge from the agent S container 1 the liquid agent S that always contains a constant concentration (saturated concentration) of sodium chloride. The liquid agent S discharged from the agent S container 1 is supplied to the second water supply line 532 by the agent S discharge pump 15 and mixed with water that flows from the supply source 5, and thus the sodium chloride concentration is suitably adjusted, and the mixture is supplied to the agent B container 2. Thereby, the liquid S-B mixture is generated in the agent B container 2. At this time, as described above, in the case where the liquid agent S is brought into contact with an excessive amount of the solid agent B, the sodium ion concentration in the resulting liquid S-B mixture is always at a constant level (saturated concentration), and bicarbonate ions contained in the liquid S-B mixture are equimolar to sodium ions derived from the solid agent B. That is, according to the sodium chloride concentration in the liquid agent S supplied to the solid agent B, the bicarbonate ion concentration in the liquid S-B mixture discharged from the agent B container 2 changes, but the sodium ion concentration can be maintained at a constant level. Note that, in order to check the concentration of the sodium chloride solution flowing through the second water supply line 532, it is desirable to provide the electric conductivity meter 91 on the second water supply line 532. The liquid S-B mixture prepared in this way is supplied to the mixing part 4 by the pump 22, and at the same time, the liquid agent A discharged from the agent A container 3 is also supplied to the mixing part 4 by the pump 32. As a result, a dialysis fluid is prepared in the mixing part 4, and this dialysis fluid is sent to the dialyzer 6. In the processes above, the pumps 13, 15, 22, 32, and 52 are controlled based on the set preparation method or the measurement results of the electric conductivity meters 9 and 91.

Third Embodiment

Figure 4:
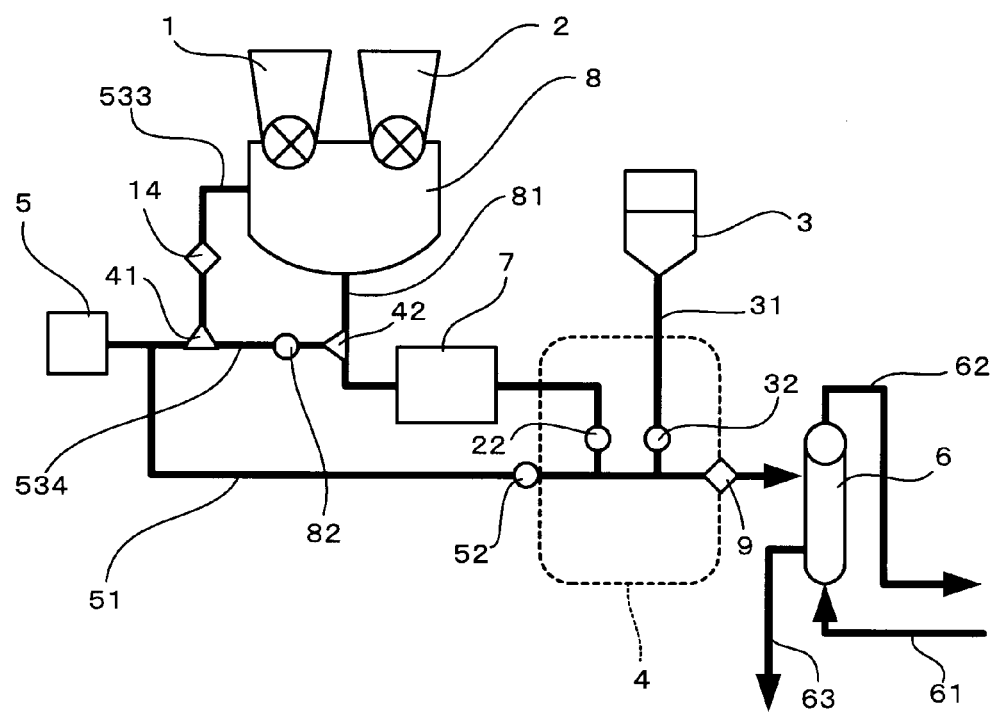
FIG. 4 is a schematic configurational diagram showing the third embodiment of a dialysis fluid preparation apparatus of the present invention.

Next, the third embodiment of the dialysis fluid preparation apparatus of the present invention will now be described in reference to FIG. 4. FIG. 4 is a schematic configurational diagram showing the third embodiment of the dialysis fluid preparation apparatus. The third embodiment also commonly shares many features with the first embodiment, and therefore, the same components as in the first embodiment are given the same numerical references unless specified otherwise, and different features will be mainly described in the following description. As shown in FIG. 4, this apparatus includes a dissolving tank 8 to which the agent S container 1 and the agent B container 2 are attached. The solid agent S and the solid agent B discharged from the outlets of the agent S container 1 and the agent B container 2, respectively, are supplied to the dissolving tank 8, and the openings of the outlets of the containers 1 and 2 are controlled by the control part to adjust the amounts of the solid agent S and the solid agent B to be supplied to the dissolving tank 8. Also, the dissolving tank 8 has an outlet, and a discharge line 81 extending from the outlet is connected to the main supply line 51 in the mixing part 4. In the middle of the discharge line 81, a storage tank 7 that temporarily stores the liquid S-B mixture discharged from the dissolving tank is provided. A water supply/circulation line 534 branches from an upstream part of the main supply line 51, and is connected to the dissolving tank 8. A first three-way valve 41 is provided in the middle of the water supply/circulation line 534, a solution circulation line 533 branches therefrom, and an electric conductivity meter 14 is provided. Also, the water supply/circulation line 534 is connected to the discharge line 81 via a second three-way valve 42. On the water supply/circulation line 534, a circulating pump 82 is provided between the first three-way valve 41 and the second three-way valve 42. A supply of water to the dissolution tank 8, circulation, and discharge of the liquid S-B mixture are, as described below, carried out by suitably opening or closing the first and second three-way valves 41 and 42 by the control part. Other configurations are the same as the first embodiment.

Next, actions of the apparatus configured as described above will now be described. First, water is caused to flow into the dissolution tank 8 from the supply source 5 by switching between the valve positions of the first three-way valve 41. Once a specific amount of water is supplied to the dissolution tank 8, the liquid S-B mixture in which the solid agent S and the solid agent B are dissolved at constant concentrations and in any desired ratio is generated in the dissolution tank 8. Next, the valve positions of the first and second three-way valves 41 and 42 are switched to cause the water supply/circulation line 534, the solution circulation line 533, the discharge line 81, and the dissolution tank 8 to be in communication, and in this state, the circulating pump 82 is driven. Thereby, the S-B mixture circulates, and the solid agent S and the solid agent B sufficiently dissolve. At this time, the concentration of the S-B mixture is measured by the electric conductivity meter 14, and adjusting the openings of the outlets of the containers 1 and 2 adjusts the concentration of the S-B mixture. Once the S-B mixture having a desired concentration is produced in this way, the valve positions of the second three-way valve 42 are switched to discharge the S-B mixture from the dissolution tank 8 to the discharge line 81. The S-B mixture thus discharged is supplied to the mixing part 4 via the storage tank 7. At the same time, the liquid agent A discharged from the agent A container 3 is also supplied to the mixing part 4. As a result, a dialysis fluid is prepared in the mixing part 4, and this dialysis fluid is sent to the dialyzer 6. In the processes above, the pumps 22, 32, and 52 are controlled based on the set preparation method or the measurement results of the electric conductivity meters 9 and 14.

In this embodiment, the liquid S-B mixture is produced in a batchwise manner in the dissolution tank 8, thus making it possible to change the bicarbonate ion concentration of a dialysis fluid in a stepwise manner (the concentration is different for every batch). That is, until the entire amount of the S-B mixture stored in the storage tank 7 is supplied to the mixing part 4, the second three-way valve 42 is closed so as not to supply any pharmaceutical ingredient from the dissolution tank 8. Then, after the entire amount of the pharmaceutical ingredient in the storage tank 7 is discharged, another S-B mixture having a different concentration is supplied to the storage tank 7 from the dissolution tank 8, thereby making it possible to supply a dialysis fluid whose concentration is changed in a stepwise manner.

Also, supplying a batch of the liquid S-B mixture to the mixing part 4 while another batch of the liquid S-B mixture remains in the storage tank 7 makes it possible to continuously change the bicarbonate ion concentration of a dialysis fluid. That is, while supplying the S-B mixture stored in the storage tank 7 to the mixing part 4, closing the second three-way valve 42 makes it possible to prepare another S-B mixture having a different bicarbonate ion concentration in the dissolution tank 8. Then, while supplying the S-B mixture in the storage tank 7 to the mixing part 4, the newly prepared S-B mixture is supplied to the storage tank 7 from the dissolution tank 8. Thereby, the bicarbonate ion concentration in the S-B mixture in the storage tank 7 changes over time, and it is possible to supply the S-B mixture that has undergone such a change to the mixing part 4. At this time, based on the concentrations of the S-B mixture present in the storage tank 7 and the S-B mixture produced in the dissolution tank 8, the openings of the pump 22 and the second three-way valve 42 are controlled, thus making it possible to change the bicarbonate ion concentration over time.

In the description above, an example in which the bicarbonate ion concentration of the S-B mixture is changed using the storage tank 7 has been presented. It is also possible to configure the storage tank 7 such that pharmaceutical ingredients are supplied from at least two of the three containers 1, 2, and 3. Thereby, it is also possible to change the component concentrations other than the bicarbonate concentration in a batchwise manner or over time. Note that the storage tank 7 is optional, and the discharge line 81 can be directly connected to the main supply line 51.

Embodiments of the dialysis fluid preparation apparatus of the present invention have been described above, but the present invention is not limited to the foregoing embodiments, and various changes can be made. For example, in the foregoing embodiments, the amounts of pharmaceutical ingredients supplied to the mixing part 4 are changed by the pumps provided on the respective lines, but it is also possible that the openings of the outlets of the containers 1, 2, and 3 are adjusted by the control part to adjust the discharge amounts and thus to achieve the desired state of a dialysis fluid. Also, it is possible that valves are provided in place of the pumps, and the openings thereof are adjusted to change the flow rates of fluids and thus to prepare a dialysis fluid.

4. Dialysis System

In one embodiment, the dialysis system of the present invention is a system for carrying out dialysis using the above-described dialysate and dialysis fluid preparation apparatus. Specifically, in one embodiment, the dialysis system of the present invention includes the above-described dialysate, the above-described dialysis fluid preparation apparatus, and a dialyzer. In one embodiment, the dialysis system of the present invention is configured such that the agent S, the agent B, and the agent A in the dialysate are accommodated in the agent S container, the agent B container, and the agent A container, respectively, of the dialysis fluid preparation apparatus, and a dialysis fluid prepared in the mixing part is sent to the dialyzer via a supply line. The dialysis fluid and blood come into contact with each other via a dialysis membrane in the dialyzer in the dialysis system of the present invention, and hemodialysis is thus carried out. In one embodiment, in the dialysis system of the present invention, the dialysis fluid preparation method, the concentrations of dialysis fluid components, and other features are as described above.

Hemodialysis Method

In one embodiment, the present invention provides a hemodialysis method comprising subjecting a patient to a hemodialysis using a dialysis fluid prepared with a dialysate. The details of the dialysate and the preparation thereof are described in "1. Dialysate and preparation of dialysis fluid" above. In this hemodialysis method, the dialysis fluid preparation apparatus or the dialysis system described above may be used. The details of the apparatus and the system are described in "3. Dialysis fluid preparation apparatus" and "4. Dialysis system" respectively.

EXAMPLES

Below, various embodiments of the present invention shall be described in detail by way of examples, but the present invention is not construed as being limited to the examples.

Example 1

A dialysis fluid was prepared according to the following method using the dialysis fluid preparation apparatus shown in FIG. 1.

26.10 g of potassium chloride, 38.59 g of calcium chloride hydrate, 17.79 g of magnesium chloride hydrate, 21.02 g of acetic acid, 86.13 g of sodium acetate, and 175 g of glucose were dissolved in water, the total volume was brought to 1000 ml, and this fluid, regarded as a liquid agent A, was accommodated in the agent A container 3. An excessive amount of sodium chloride (solid) was introduced into the agent S container 1, and water at 25° C. that had been treated with a reverse osmosis membrane (hereinafter referred to as "RO water") was supplied to the agent S container 1, thus giving a liquid agent S having a saturated sodium chloride concentration of 31 g/100 ml in the agent S container 1. An excessive amount of sodium bicarbonate (solid) was introduced into the agent B container 2, and RO water was supplied thereto, thus giving a liquid agent B having a saturated sodium bicarbonate concentration of 10 g/100 ml in the agent B container 2.

The rates of supplying the liquid agent S, the liquid agent B, the liquid agent A, and water to the mixing part 4 were controlled as shown in Table 2, thus giving a dialysis fluid whose bicarbonate ion concentration was changed over time and sodium ion concentration was maintained at a constant level. Potassium ions, calcium ions, magnesium ions, acetate ions, and glucose in the dialysis fluid were set at constant levels as shown in Table 3. Specifically, for 40 minutes from the beginning of dialysis fluid preparation, the sodium ion concentration of the final dialysis fluid was set at 140 mEq/l, the bicarbonate ion concentration thereof was set at 30 mEq/l, the rate of supplying the liquid agent S (the flow rate of the pump 12) was 6.86 ml/min, the rate of supplying the liquid agent B (the flow rate of the pump 22) was 8.82 ml/min, the rate of supplying the liquid agent A (the flow rate of the pump 32) was 2.00 ml/min, and the rate of supplying RO water (the flow rate of the pump 52) was 332.32 ml/min. From 40 minutes to 80 minutes after the beginning of dialysis fluid preparation, the sodium ion concentration of the final dialysis fluid was set at 140 mEq/l, the bicarbonate ion concentration thereof was set at 25 mEq/l, the rate of supplying the liquid agent S (the flow rate of the pump 12) was 7.19 ml/min, the rate of supplying the liquid agent B (the flow rate of the pump 22) was 7.35 ml/min, the rate of supplying the liquid agent A (the flow rate of the pump 32) was 2.00 ml/min, and the rate of supplying RO water (the flow rate of the pump 52) was 333.46 ml/min. From 80 minutes to 120 minutes after the beginning of dialysis fluid preparation, the sodium ion concentration of the final dialysis fluid was set at 140 mEq/l, the bicarbonate ion concentration thereof was set at 20 mEq/l, the rate of supplying the liquid agent S (the flow rate of the pump 12) was 7.52 ml/min, the rate of supplying the liquid agent B (the flow rate of the pump 22) was 5.88 ml/min, the rate of supplying the liquid agent A (the flow rate of the pump 32) was 2.00 ml/min, and the rate of supplying RO water (the flow rate of the pump 52) was 334.60 ml/min. From 120 minutes to 160 minutes after the beginning of dialysis fluid preparation, the sodium ion concentration of the final dialysis fluid was set at 140 mEq/l, the bicarbonate ion concentration thereof was set at 35 mEq/l, the rate of supplying the liquid agent S (the flow rate of the pump 12) was 6.53 ml/min, the rate of supplying the liquid agent B (the flow rate of the pump 22) was 10.29 ml/min, the rate of supplying the liquid agent A (the flow rate of the pump 32) was 2.00 ml/min, and the rate of supplying RO water (the flow rate of the pump 52) was 331.18 ml/min. From 160 minutes to 200 minutes after the beginning of dialysis fluid preparation, the sodium ion concentration of the final dialysis fluid was set at 140 mEq/l, the bicarbonate ion concentration thereof was set at 40 mEq/l, the rate of supplying the liquid agent S (the flow rate of the pump 12) was 6.20 ml/min, the rate of supplying the liquid agent B (the flow rate of the pump 22) was 11.76 ml/min, the rate of supplying the liquid agent A (the flow rate of the pump 32) was 2.00 ml/min, and the rate of supplying RO water (the flow rate of the pump 52) was 330.04 ml/min. During dialysis fluid preparation, the dialysis fluid prepared in the mixing part 4 was continuously discharged out of the mixing part 4 at a flow rate of 350 ml/min.

TABLE 2

| | Set concentration of dialysis fluid (mEq/l) | | Control condition of each pump | | | |
|---|---|---|---|---|---|---|
| Time (min) | Bi-carbon-ate ion | Sodium ion | Rate of supplying liquid agent S (ml/min) | Rate of supplying liquid agent B (ml/min) | Rate of supplying liquid agent A (ml/min) | Rate of supplying RO water (ml/min) |
| 0-40 | 30 | 140 | 6.86 | 8.82 | 2.00 | 332.32 |
| 40-80 | 25 | 140 | 7.19 | 7.35 | 2.00 | 333.46 |
| 80-120 | 20 | 140 | 7.52 | 5.88 | 2.00 | 334.60 |
| 120-160 | 35 | 140 | 6.53 | 10.29 | 2.00 | 331.18 |
| 160-200 | 40 | 140 | 6.20 | 11.76 | 2.00 | 330.04 |

TABLE 3

| | Set concentration of each dialysis fluid component (other than bicarbonate ion and sodium ion) |
|---|---|
| Calcium ion | 3 mEq/l |
| Potassium ion | 2 mEq/l |
| Magnesium ion | 1 mEq/l |
| Acetate ion | 8 mEq/l |
| Glucose | 1 g/l |

The prepared dialysis fluid was sampled over time, and the composition of the dialysis fluid was analyzed. Specifically, the bicarbonate ion concentration, the pH, and the osmotic pressure of the dialysis fluid were measured by a blood gas and electrolyte analyzer (cobas b121), and the concentrations of sodium ions, potassium ions, calcium ions, and magnesium ions of the dialysis fluid were measured by ion chromatography. The acetic acid and glucose concentrations of the dialysis fluid were measured by high performance liquid chromatography.

Figure 5:
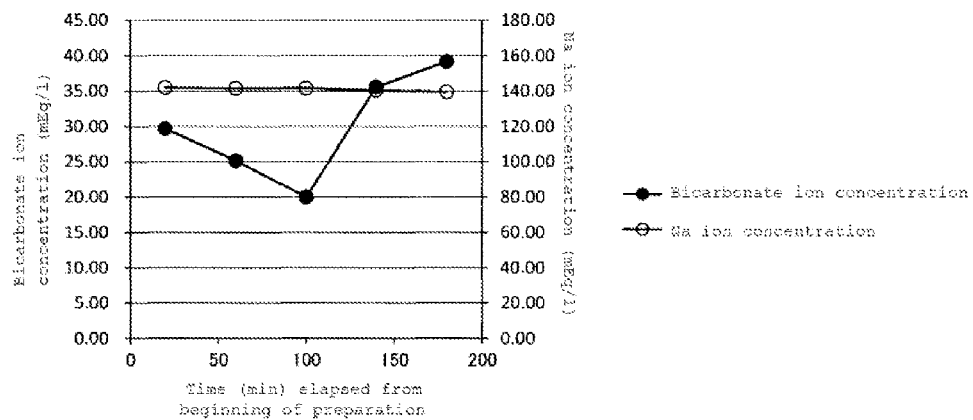
FIG. 5 is a diagram showing the results of measuring over time the bicarbonate ion concentration and the sodium ion concentration of the dialysis fluid prepared in Example 1.

The obtained results are shown in Table 4 and FIG. 5. It is clear from the results that adjusting the rate of supplying the liquid agent B makes it possible to change the concentration of bicarbonate ions of the dialysis fluid, and adjusting the rates of supplying the liquid agent S and RO water according to the rate of supplying the liquid agent B makes it possible to maintain the sodium ion concentration of the dialysis fluid at a constant level. It was also confirmed that, under the conditions of Example 1, the concentrations of other components such as potassium ions, calcium ions, magnesium ions, acetic acid, and glucose are maintained at constant levels, and the pH also is controlled to be within an optimum range.

TABLE 4

Results of analyzing prepared dialysis fluid

| | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid 20 minutes after beginning of preparation | 29.70 | 14.0 | 7.37 | 306.5 | 141.99 | 2.02 | 3.00 | 1.01 | 7.97 | 0.99 |
| Dialysis fluid 60 minutes after beginning of preparation | 25.15 | 14.2 | 7.37 | 307.5 | 141.54 | 2.03 | 3.06 | 0.99 | 8.03 | 0.99 |
| Dialysis fluid 100 minutes after beginning of preparation | 19.98 | 14.3 | 7.34 | 308.8 | 141.64 | 2.02 | 3.03 | 1.02 | 8.00 | 0.99 |

TABLE 4-continued

Results of analyzing prepared dialysis fluid

|  | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid 140 minutes after beginning of preparation | 35.59 | 13.9 | 7.41 | 305.2 | 140.52 | 2.01 | 3.04 | 1.01 | 7.93 | 0.99 |
| Dialysis fluid 180 minutes after beginning of preparation | 39.15 | 13.7 | 7.45 | 305.2 | 139.51 | 1.98 | 2.98 | 1.00 | 7.92 | 0.98 |

Example 2

A dialysis fluid was prepared according to the following method using the dialysis fluid preparation apparatus shown in FIG. 1.

The liquid agent A as used in Example 1 was accommodated in the agent A container 3. An excessive amount of sodium chloride (solid) was introduced into the agent S container 1, and water at 25° C. that had been treated with a reverse osmosis membrane (hereinafter referred to as "RO water") was supplied to the agent S container 1, thus giving a liquid agent S having a saturated sodium chloride concentration of 31 g/100 ml in the agent S container 1. An excessive amount of sodium bicarbonate (solid) was introduced into the agent B container 2, and RO water was supplied thereto, thus giving a liquid agent B having a saturated sodium bicarbonate concentration of 10 g/100 ml in the agent B container 2.

The rates of supplying the liquid agent S, the liquid agent B, the liquid agent A, and water to the mixing part 4 were controlled as shown in Table 5, thus giving a dialysis fluid whose bicarbonate ion concentration and sodium ion concentration were changed over time. Potassium ions, calcium ions, magnesium ions, acetate ions, and glucose in the dialysis fluid were set at constant levels as shown in Table 3 above. Specifically, for 40 minutes from the beginning of dialysis fluid preparation, the sodium ion concentration of the final dialysis fluid was set at 150 mEq/l, the bicarbonate ion concentration thereof was set at 25 mEq/l, the rate of supplying the liquid agent S (the flow rate of the pump 12) was 7.85 ml/min, the rate of supplying the liquid agent B (the flow rate of the pump 22) was 7.35 ml/min, the rate of supplying the liquid agent A (the flow rate of the pump 32) was 2.00 ml/min, and the rate of supplying RO water (the flow rate of the pump 52) was 332.80 ml/min. From 40 minutes to 80 minutes after the beginning of dialysis fluid preparation, the sodium ion concentration of the final dialysis fluid was set at 145 mEq/l, the bicarbonate ion concentration thereof was set at 30 mEq/l, the rate of supplying the liquid agent S (the flow rate of the pump 12) was 7.19 ml/min, the rate of supplying the liquid agent B (the flow rate of the pump 22) was 8.82 ml/min, the rate of supplying the liquid agent A (the flow rate of the pump 32) was 2.00 ml/min, and the rate of supplying RO water (the flow rate of the pump 52) was 331.99 ml/min. From 80 minutes to 120 minutes after the beginning of dialysis fluid preparation, the sodium ion concentration of the final dialysis fluid was set at 140 mEq/l, the bicarbonate ion concentration thereof was set at 35 mEq/l, the rate of supplying the liquid agent S (the flow rate of the pump 12) was 6.53 ml/min, the rate of supplying the liquid agent B (the flow rate of the pump 22) was 10.29 ml/min, the rate of supplying the liquid agent A (the flow rate of the pump 32) was 2.00 ml/min, and the rate of supplying RO water (the flow rate of the pump 52) was 331.18 ml/min. During dialysis fluid preparation, the dialysis fluid prepared in the mixing part 4 was continuously discharged out of the mixing part 4 at a flow rate of 350 ml/min.

TABLE 5

| | Set concentration of dialysis fluid (mEq/l) | | Control condition of each pump | | | |
|---|---|---|---|---|---|---|
| Time (min) | Bi-carbon-ate ion | Sodium ion | Rate of supplying liquid agent S (ml/min) | Rate of supplying liquid agent B (ml/min) | Rate of supplying liquid agent A (ml/min) | Rate of supplying RO water (ml/min) |
| 0-40 | 25 | 150 | 7.85 | 7.35 | 2.00 | 332.80 |
| 40-80 | 30 | 145 | 7.19 | 8.82 | 2.00 | 331.99 |
| 80-120 | 35 | 140 | 6.53 | 10.29 | 2.00 | 331.18 |

The prepared dialysis fluid was sampled over time, and the composition of the dialysis fluid was analyzed in the same manner as in Example 1.

Figure 6:
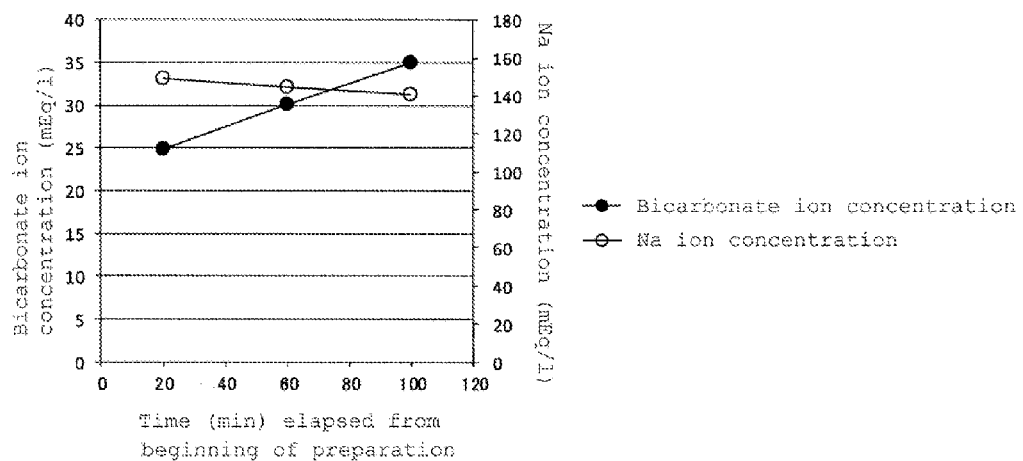
FIG. 6 is a diagram showing the results of measuring over time the bicarbonate ion concentration and the sodium ion concentration of the dialysis fluid prepared in Example 2.

The obtained results are shown in Table. 6 and FIG. 6. It was confirmed from the results that adjusting the rates of supplying the liquid agent S and the liquid agent B makes it possible to change the bicarbonate ion concentration of the dialysis fluid and also the sodium ion concentration of the dialysis fluid. It was also confirmed that, under the conditions of Example 2, the concentrations of other components such as potassium ions, calcium ions, magnesium ions, acetic acid, and glucose are maintained at constant levels, and the pH also is controlled to be within an optimum range.

TABLE 6

|  | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid 20 minutes after beginning of preparation | 24.93 | 14.9 | 7.31 | 321.5 | 149.36 | 1.98 | 2.97 | 0.97 | 7.98 | 1.00 |
| Dialysis fluid 60 minutes after beginning of preparation | 30.04 | 14.5 | 7.39 | 309.0 | 144.67 | 1.98 | 2.99 | 0.98 | 7.99 | 1.00 |
| Dialysis fluid 100 minutes after beginning of preparation | 34.98 | 13.8 | 7.43 | 299.6 | 140.65 | 2.01 | 3.03 | 1.01 | 8.04 | 1.02 |

Example 3

A dialysis fluid was prepared according to the following method using the dialysis fluid preparation apparatus shown in FIG. 3.

The liquid agent A as used in Example 1 was accommodated in the agent A container 3. An excessive amount of sodium chloride (solid) was introduced into the agent S container 1, and RO water at 25° C. was supplied thereto, thus giving a liquid agent S having a saturated sodium chloride concentration of 31 g/100 ml in the agent S container 1. Also, an excessive amount of sodium bicarbonate (solid agent B) was accommodated in the agent B container 2.

As shown in Table 7, the ratio of the liquid agent S discharged from the agent S container 1 relative to RO water was controlled to change the sodium chloride concentration of the liquid agent S brought into contact with the solid agent B, and the ratio between the S-B mixture (liquid), the liquid agent A, and RO water supplied to the mixing part 4 was controlled, thus giving a dialysis fluid whose bicarbonate ion concentration was changed over time and sodium ion concentration was maintained at a constant level. Potassium ions, calcium ions, magnesium ions, acetate ions, and glucose in the dialysis fluid were set at constant levels as shown in Table 3 above. Specifically, for 40 minutes from the beginning of dialysis fluid preparation, the sodium ion concentration of the final dialysis fluid was set at 140 mEq/l, the bicarbonate ion concentration thereof was set at 20 mEq/l, the sodium chloride concentration of the liquid agent S brought into contact with the solid agent B was adjusted to 13.99 g/100 ml by the pump 13, the rate of supplying the S-B mixture (the flow rate of the pump 22) was 16.67 ml/min, the rate of supplying the liquid agent A (the flow rate of the pump 32) was 2.00 ml/min, and the rate of supplying RO water (the flow rate of the pump 52) was 331.33 ml/min. From 40 minutes to 80 minutes after the beginning of dialysis fluid preparation, the sodium chloride concentration of the liquid agent S brought into contact with the solid agent B was changed to 10.00 g/100 ml by the pump 13, the rate of supplying the S-B mixture (the flow rate of the pump 22) was 21.28 ml/min, the rate of supplying the liquid agent A (the flow rate of the pump 32) was 2.00 ml/min, and the rate of supplying RO water (the flow rate of the pump 52) was changed to 326.72 ml/min. From 80 minutes to 120 minutes after the beginning of dialysis fluid preparation, the sodium chloride concentration of the liquid agent S brought into contact with the solid agent B was changed to 8.08 g/100 ml by the pump 13, the rate of supplying the S-B mixture (the flow rate of the pump 22) was 23.81 ml/min, the rate of supplying the liquid agent A (the flow rate of the pump 32) was 2.00 ml/min, and the rate of supplying RO water (the flow rate of the pump 52) was changed to 324.19 ml/min. During dialysis fluid preparation, the dialysis fluid prepared in the mixing part 4 was continuously discharged out of the mixing part 4 at a flow rate of 350 ml/min.

TABLE 7

| | Set concentration of dialysis fluid (mEq/l) | | Sodium chloride concentration (g/100 ml) of liquid agent S[#1] brought into contact with solid agent B | Control condition of each pump | | |
|---|---|---|---|---|---|---|
| | | | | Rate of supplying S-B | Rate of supplying liquid | Rate of supplying |
| Time (min) | Bicarbonate ion | Sodium ion | | mixture (ml/min) | agent A (ml/min) | RO water (ml/min) |
| 0-40 | 20 | 140 | 13.99 | 16.67 | 2.00 | 331.33 |
| 40-80 | 30 | 140 | 10.00 | 21.28 | 2.00 | 326.72 |
| 80-120 | 40 | 140 | 8.08 | 23.81 | 2.00 | 324.19 |

[#1]The sodium chloride concentration of the liquid agent S brought into contact with the solid agent B was controlled by adjusting the rate of supplying RO water by the pump 13 and the rate of supplying the liquid agent S discharged from the agent S container 1 by the pump 15.

The prepared dialysis fluid was sampled over time, and the composition of the dialysis fluid was analyzed in the same manner as in Example 1.

Figure 7:
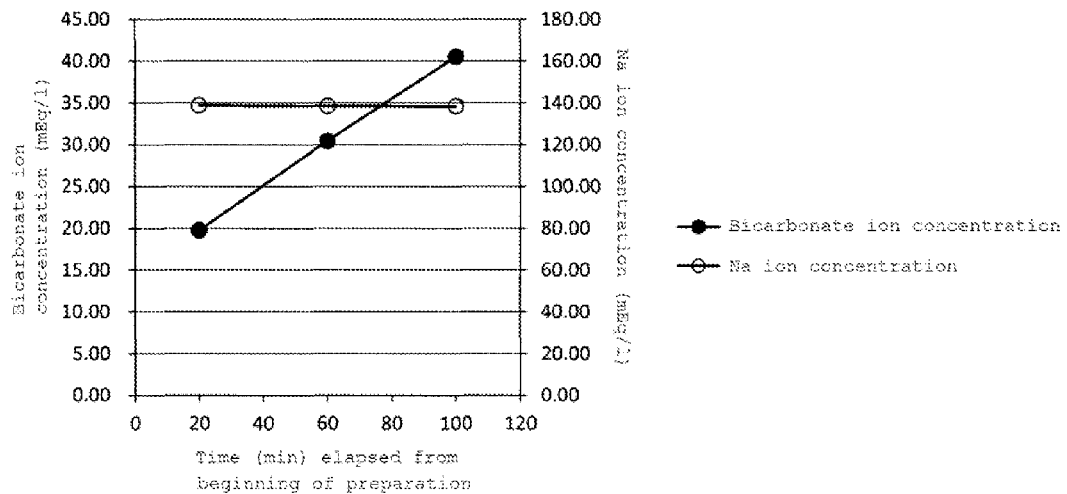
FIG. 7 is a diagram showing the results of measuring over time the bicarbonate ion concentration and the sodium ion concentration of the dialysis fluid prepared in Example 3.

The obtained results are shown in Table 8 and FIG. 7. It is clear from the results that adjusting the concentration of the liquid agent S brought into contact with the solid agent B makes it possible to change the bicarbonate ion concentration of the dialysis fluid, and adjusting the rates of supplying the liquid agent S, the S-B mixture, and RO water makes it possible to maintain the sodium ion concentration of the dialysis fluid at a constant level. It was also confirmed that, under the conditions of Example 3, the concentrations of other components such as potassium ions, calcium ions, magnesium ions, acetic acid, and glucose are maintained at constant levels, and the pH also can be controlled to be within an optimum range.

constant levels as shown in Table 3 above. Specifically, for 40 minutes from the beginning of dialysis fluid preparation, the sodium ion concentration of the final dialysis fluid was set at 150 mEq/l, the bicarbonate ion concentration thereof was set at 25 mEq/l, the sodium chloride concentration of the liquid agent S brought into contact with the solid agent B was adjusted to 11.90 g/100 ml by the pump 13, the rate of supplying the S-B mixture (the flow rate of the pump 22) was 20.46 ml/min, the rate of supplying the liquid agent A (the flow rate of the pump 32) was 2.00 ml/min, and the rate of supplying RO water (the flow rate of the pump 52) was 327.54 ml/min. From 40 minutes to 80 minutes after the beginning of dialysis fluid preparation, the sodium ion concentration and the bicarbonate ion concentration of the dialysis fluid were set at 145 mEq/l and 30 mEq/l, respectively, the sodium chloride concentration of the liquid agent

TABLE 8

Results of analyzing prepared dialysis fluid

| | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid 20 minutes after beginning of preparation | 19.76 | 14.0 | 7.32 | 302.8 | 138.80 | 2.01 | 3.01 | 0.99 | 8.08 | 1.00 |
| Dialysis fluid 60 minutes after beginning of preparation | 30.43 | 14.0 | 7.42 | 297.3 | 138.49 | 1.98 | 2.99 | 1.00 | 7.95 | 0.99 |
| Dialysis fluid 100 minutes after beginning of preparation | 40.54 | 13.6 | 7.46 | 295.3 | 138.47 | 2.02 | 3.02 | 1.01 | 8.07 | 1.00 |

Example 4

A dialysis fluid was prepared according to the following method using the dialysis fluid preparation apparatus shown in FIG. 3. The liquid agent A as used in Example 1 was accommodated in the agent A container 3. An excessive amount of sodium chloride (solid) was introduced into the agent S container 1, and RO water at 25° C. was supplied thereto, thus giving a liquid agent S having a saturated sodium chloride concentration of 31 g/100 ml in the agent S container 1. Also, an excessive amount of sodium bicarbonate (solid agent B) was accommodated in the agent B container 2.

As shown in Table 9, the ratio of the liquid agent S discharged from the agent S container 1 relative to RO water was controlled to change the sodium chloride concentration of the liquid agent S brought into contact with the solid agent B, and the ratio between the S-B mixture (liquid), the liquid agent A, and RO water supplied to the mixing part 4 was controlled, thus giving a dialysis fluid whose bicarbonate ion concentration and sodium ion concentration were changed over time. Potassium ions, calcium ions, magnesium ions, acetate ions, and glucose in the dialysis fluid were set at S brought into contact with the solid agent B was changed to 10.40 g/100 ml by the pump 13, the rate of supplying the S-B mixture (the flow rate of the pump 22) was 21.43 ml/min, the rate of supplying the liquid agent A (the flow rate of the pump 32) was 2.00 ml/min, and the rate of supplying RO water (the flow rate of the pump 52) was changed to 326.57 ml/min. From 80 minutes to 120 minutes after the beginning of dialysis fluid preparation, the sodium ion concentration and the bicarbonate ion concentration of the dialysis fluid were set at 140 mEq/l and 35 mEq/l, respectively, the sodium chloride concentration of the liquid agent S brought into contact with the solid agent B was changed to 8.80 g/100 ml by the pump 13, the rate of supplying the S-B mixture (the flow rate of the pump 22) was 23.01 ml/min, the rate of supplying the liquid agent A (the flow rate of the pump 32) was 2.00 ml/min, and the rate of supplying RO water (the flow rate of the pump 52) was changed to 324.99 ml/min. During dialysis fluid preparation, the dialysis fluid prepared in the mixing part 4 was continuously discharged out of the mixing part 4 at a flow rate of 350 ml/min.

TABLE 9

| Time (min) | Set concentration of dialysis fluid (mEq/l) Bicarbonate ion | Set concentration of dialysis fluid (mEq/l) Sodium ion | Sodium chloride concentration (g/100 ml) of liquid agent S[#1] brought into contact with solid agent B | Control condition of each pump Rate of supplying S-B mixture (ml/min) | Control condition of each pump Rate of supplying liquid agent A (ml/min) | Control condition of each pump Rate of supplying RO water (ml/min) |
|---|---|---|---|---|---|---|
| 0-40 | 25 | 150 | 11.90 | 20.46 | 2.00 | 327.54 |
| 40-80 | 30 | 145 | 10.40 | 21.43 | 2.00 | 326.57 |
| 80-120 | 35 | 140 | 8.80 | 23.01 | 2.00 | 324.99 |

[#1]The sodium chloride concentration of the liquid agent S brought into contact with the solid agent B was controlled by adjusting the rate of supplying RO water by the pump 13 and the rate of supplying the liquid agent S discharged from the agent S container 1 by the pump 15.

The prepared dialysis fluid was sampled over time, and the composition of the dialysis fluid was analyzed in the same manner as in Example 1.

Figure 8:
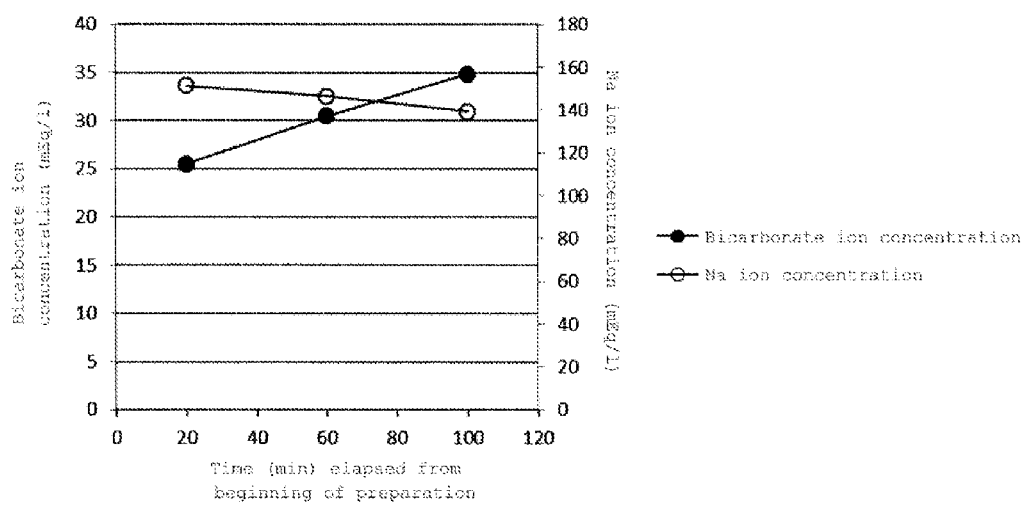
FIG. 8 is a diagram showing the results of measuring over time the bicarbonate ion concentration and the sodium ion concentration of the dialysis fluid prepared in Example 4.

The obtained results are shown in Table 10 and FIG. 8. It was confirmed from the results that adjusting the concentration of the liquid agent S brought into contact with the solid agent B and the rates of supplying the S-B mixture and RO water makes it possible to change the bicarbonate ion concentration of the dialysis fluid and also the sodium ion concentration of the dialysis fluid. It was also confirmed that, under the conditions of Example 4, the concentrations of other components such as potassium ions, calcium ions, magnesium ions, acetic acid, and glucose are maintained at constant levels, and the pH also can be controlled to be within an optimum range.

Next, as described below, the agent S, the agent B, and RO water were supplied to the dissolution tank 8, and a liquid S-B mixture was prepared in the dissolution tank. Also, as described below, the ratio between the S-B mixture (liquid), the liquid agent A, and RO water supplied to the mixing part 4 was controlled, thus giving a dialysis fluid whose bicarbonate ion concentration was changed in a batchwise manner and sodium ion concentration was maintained at a constant level. Potassium ions, calcium ions, magnesium ions, acetate ions, and glucose in the dialysis fluid were set at constant levels as shown in Table 3 above.

First, the sodium ion concentration of the final dialysis fluid was set at 140 mEq/l and the bicarbonate ion concentration thereof was set at 40 mEq/l, and control was carried out as follows. Pieces of the solid agent S were introduced

TABLE 10

| | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid 20 minutes after beginning of preparation | 25.48 | 15.0 | 7.32 | 325.8 | 151.44 | 2.01 | 3.01 | 1.02 | 8.01 | 1.01 |
| Dialysis fluid 60 minutes after beginning of preparation | 30.48 | 14.5 | 7.39 | 313.7 | 146.47 | 2.02 | 3.00 | 1.01 | 8.00 | 1.01 |
| Dialysis fluid 100 minutes after beginning of preparation | 34.87 | 13.8 | 7.42 | 297.5 | 139.36 | 1.98 | 2.98 | 0.99 | 7.97 | 1.00 |

Example 5

A dialysis fluid was prepared according to the following method using the dialysis fluid preparation apparatus shown in FIG. 4. The liquid agent A as used in Example 1 was accommodated in the agent A container 3. Sodium chloride (solid) was introduced into the agent S container 1, and sodium bicarbonate (solid) was introduced into the agent B container 2.

from the agent S container 1 into the dissolution tank 8 to which RO water at 25° C. had been supplied using the pump 82, the aqueous solution was circulated through the line 533, the line 534, and the dissolution tank 8 using the pump 82, the concentration was managed in reference to the electric conductivity meter 14, and introduction was terminated when the conductivity reached 80.9 mS/cm. Then, Pieces of the solid agent B were introduced from the agent B container 2 into the agent S solution, the aqueous solution was circulated in the same manner, and introduction was terminated when the conductivity reached 93.1 mS/cm. The flow rate of the pump 22 that supplies the liquid S-B mixture produced in this manner was set at 35.00 ml/min, the flow rate of the pump 32 was set at 2.00 ml/min, and the flow rate of the pump 52 was set at 313.00 ml/min, thus giving a dialysis fluid (first batch).

Next, the sodium ion concentration of the final dialysis fluid was set at 140 mEq/l and the bicarbonate ion concentration thereof was set at 30 mEq/l, and control was carried out as follows. After the entire amount of the liquid S-B mixture was supplied from the dissolution tank 8 to the mixing part 4, RO water at 25° C. was again supplied to the dissolution tank 8 using the pump 82 to start preparing the second batch of the dialysis fluid. The same procedure as the above-described first batch was followed except that, in order to change the bicarbonate ion concentration to 30 mEq/l, the setting value of conductivity of the agent S solution determined by the electric conductivity meter 14 was changed to 88.1 mS/cm and that of the liquid S-B mixture was changed to 97.0 mS/cm, thus giving a dialysis fluid (second batch).

Moreover, the sodium ion concentration of the final dialysis fluid was set at 140 mEq/l and the bicarbonate ion concentration thereof was set at 20 mEq/l, and control was carried out as follows. The same procedure as the above-described first batch was followed except that the setting value of conductivity of the agent S solution determined by the electric conductivity meter 14 was changed to 94.3 mS/cm and that of the liquid S-B mixture was changed to 100.3 mS/cm, thus giving a dialysis fluid (third batch).

The composition of the prepared dialysis fluid was analyzed in the same manner as in Example 1.

Figure 9:
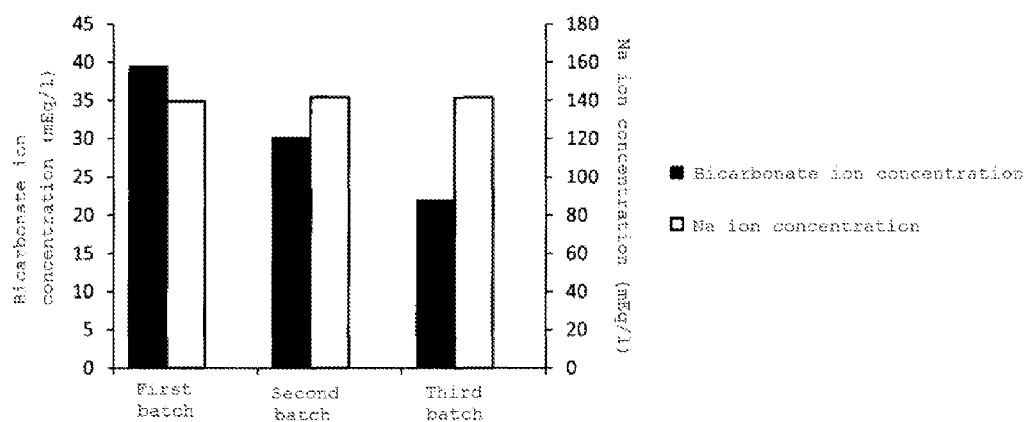
FIG. 9 is a diagram showing the results of the bicarbonate ion concentration and the sodium ion concentration of the first batch, the second batch, and the third batch of the dialysis fluid prepared in Example 5.

The obtained results are shown in Table 11 and FIG. 9. It is clear also from the results that the amount of the agent B can change the bicarbonate ion concentration of the dialysis fluid, and adjusting the amount of the agent S can maintain the sodium ion concentration of the dialysis fluid at a constant level. It was also confirmed that, under the conditions of Example 5, the concentrations of other components such as potassium ions, calcium ions, magnesium ions, acetic acid, and glucose are maintained at constant levels, and the pH also is controlled to be within an optimum range.

Comparative Example 1

A dialysis fluid was prepared according to the following method using a conventional two-component dialysate composed of a comparative agent A and an agent B described below.

106.36 g of sodium chloride, 2.61 g of potassium chloride, 3.86 g of calcium chloride hydrate, 1.78 g of magnesium chloride hydrate, 2.10 g of acetic acid, 8.61 g of sodium acetate, and 17.50 g of glucose were dissolved in water, the total volume was brought to 500 ml, and this fluid was regarded as a comparative agent A. Sodium bicarbonate powder was regarded as an agent B.

The comparative agent A, the agent B, and RO water were mixed under the conditions shown in Table 12 below, so the amount of agent B added was changed so as to correspond to 20, 30, and 40 mEq/l, thus giving dialysis fluids.

TABLE 12

|  | Set concentration of bicarbonate ion in dialysis fluid (mEq/L) | Comparative agent A | Agent B | RO water |
| --- | --- | --- | --- | --- |
| Condition 1 | 40 | 10 ml | 1.176 g | Prepared so as to |
| Condition 2 | 30 | 10 ml | 0.882 g | have a total |
| Condition 3 | 20 | 10 ml | 0.588 g | volume of 350 ml |

The compositions of the dialysis fluids prepared under conditions 1 to 3 were analyzed in the same manner as in Example 1.

The obtained results are shown in Table 13. It was confirmed from the results that with a conventional two-component dialysate, the bicarbonate ion concentration of a dialysis fluid can be changed by changing the amount of the agent B, but as the amount of the agent B is changed, the sodium ion concentration is also changed inevitably.

TABLE 11

Results of analyzing prepared dialysis fluid

| | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
| --- | --- | --- | --- | --- | --- | --- | --- | --- | --- | --- |
| First batch | 40.09 | 13.6 | 7.48 | 297.8 | 139.94 | 1.99 | 2.98 | 0.99 | 7.99 | 1.00 |
| Second batch | 30.43 | 14.0 | 7.42 | 299.7 | 140.26 | 1.99 | 2.99 | 0.99 | 8.00 | 1.00 |
| Third batch | 20.37 | 14.1 | 7.30 | 297.5 | 140.37 | 2.00 | 3.03 | 1.01 | 8.00 | 1.01 |

TABLE 13

Results of analyzing prepared dialysis fluid

| | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid of condition 1 | 39.5 | 14.6 | 7.49 | 317.9 | 150.01 | 2.01 | 3.05 | 1.01 | 8.04 | 1.00 |
| Dialysis fluid of condition 2 | 29.8 | 14.0 | 7.37 | 300.4 | 140.84 | 2.01 | 3.03 | 1.00 | 8.01 | 1.00 |
| Dialysis fluid of condition 3 | 19.8 | 13.4 | 7.26 | 283.2 | 130.79 | 2.01 | 3.02 | 0.99 | 7.97 | 1.00 |

Comparative Example 2

Dialysis fluids were prepared using a conventional two-component dialysate as used in Comparative Example 1. In Comparative Example 2, as shown in Table 14, the amount of the agent B was changed to change the bicarbonate ion concentration of the dialysis fluids, and the amount of the comparative agent A was adjusted so as to maintain the sodium ion concentration at a constant level.

TABLE 14

| | Set NaHCO$_3$ concentration | Comparative agent A | Agent B | RO water |
|---|---|---|---|---|
| Condition 4 | 40 mEq/L | 9.09 ml | 1.176 g | Prepared so as to have a total volume of 350 ml |
| Condition 5 | 30 mEq/L | 10.00 ml | 0.882 g | |
| Condition 6 | 20 mEq/L | 10.91 ml | 0.588 g | |

The compositions of the dialysis fluids prepared under conditions 4 to 6 were analyzed in the same manner as in Example 1.

The obtained results are shown in Table 15. It was confirmed from the results that with a conventional two-component dialysate, adjusting the amounts of the agent B and the comparative agent A makes it possible to change the bicarbonate ion concentration of the dialysis fluids and maintain the sodium ion concentration at a constant level, but the concentrations of other components such as potassium ions, calcium ions, magnesium ions, acetic acid, and glucose are changed, and the pH also is greatly changed.

Embodiments of the invention have are described above. While the structure has been described in terms of certain specific embodiments, there is no intention to limit the invention to the same. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

REFERENCE SIGNS LIST 1 agent S container
2 agent B container
3 agent A container
4 mixing part
5 supply source that supplies water
6 dialyzer
7 storage tank
12, 13, 15, 22, 32, 52, 82 pump
9, 14, 91 electric conductivity meter
41, 42 three-way valve

What is claimed is:
1. A hemodialysis method comprising subjecting a patient to a hemodialysis using a dialysis fluid prepared with a dialysate, wherein the dialysate is a three-component dialysate and comprises:
   an agent S containing sodium chloride,
   an agent B containing sodium bicarbonate, and
   an agent A containing electrolyte components other than sodium chloride and sodium bicarbonate,

TABLE 15

Results of analyzing prepared dialysis fluid

| | Bicarbonate ion concentration (mEq/l) | Conductivity (mS/cm) | pH | Osmotic pressure (mOsm/kg) | Na ion concentration (mEq/l) | K ion concentration (mEq/l) | Ca ion concentration (mEq/l) | Mg ion concentration (mEq/l) | Acetate ion concentration (mEq/l) | Glucose (g/l) |
|---|---|---|---|---|---|---|---|---|---|---|
| Dialysis fluid of condition 4 | 39.8 | 13.4 | 7.52 | 296.3 | 141.58 | 1.84 | 2.77 | 0.92 | 7.28 | 0.91 |
| Dialysis fluid of condition 5 | 29.8 | 14.0 | 7.37 | 300.4 | 140.84 | 2.01 | 3.03 | 1.00 | 8.01 | 1.00 |
| Dialysis fluid of condition 6 | 19.9 | 14.3 | 7.25 | 307.0 | 141.23 | 2.22 | 3.33 | 1.09 | 8.75 | 1.10 | wherein the dialysate is used such that a ratio between amounts of the agent S and the agent B is adjusted during dialysis according to a disease state of the patient so as to change a bicarbonate ion concentration and to maintain a sodium ion concentration at a constant level in the dialysis fluid, wherein the change of the bicarbonate ion concentration and the maintaining of the sodium ion concentration are set before actual start of dialysis, and wherein the patient has metabolic acidosis, and the patient is subjected to the hemodialysis in order to ameliorate the metabolic acidosis.

2. The hemodialysis method according to claim 1, wherein the dialysate is used such that the bicarbonate ion concentration in the dialysis fluid is within a range of 20 to 40 mEq/l.

3. The hemodialysis method according to claim 1, wherein the dialysate is used such that the bicarbonate ion concentration in the dialysis fluid is within a range of 25 to 35 mEq/l.

4. The hemodialysis method according to claim 1, wherein the agent S is solid.

5. The hemodialysis method according to claim 1, wherein the agent B is solid.

6. The hemodialysis method according to claim 1, wherein the agent A contains neither acetic acid nor a salt thereof.

7. The hemodialysis method according to claim 1, wherein the agent A contains an electrolyte components mixture other than sodium chloride and sodium bicarbonate.

8. A method for operating a dialysis fluid preparation apparatus including an agent S container that accommodates an agent S containing sodium chloride and has an outlet, an agent B container that accommodates an agent B containing sodium bicarbonate and has an outlet, an agent A container that accommodates an agent A containing electrolyte components other than sodium chloride and sodium bicarbonate and has an outlet, a mixing part in which the agent S discharged from the agent S container, the agent B discharged from the agent B container, and the agent A discharged from the agent A container are mixed to give a dialysis fluid, an input part that receives an input of dialysis fluid data containing bicarbonate concentration information that specifies a bicarbonate ion concentration in the dialysis fluid before actual start of dialysis, and a control part that controls at least an amount of the agent B supplied to the mixing part based on the dialysis fluid data set according to a disease state of a patient before actual start of dialysis, so as to change the bicarbonate ion concentration in the dialysis fluid during dialysis, wherein the control part operates such that a ratio between amounts of the agent S and the agent B is adjusted so as to change a bicarbonate ion concentration and to maintain a sodium ion concentration at a constant level in the dialysis fluid, wherein the disease state of the patient before start of dialysis comprises metabolic acidosis.

9. The method for operating a dialysis fluid preparation apparatus according to claim 8, wherein the control part operates so as to mix the agent S with the agent B to give an S-B mixture containing sodium chloride and sodium bicarbonate, and mix the S-B mixture with the agent A.

10. The method for operating a dialysis fluid preparation apparatus according to claim 8, wherein the control part operates so as to bring the agent S in an aqueous solution form into contact with the agent B in a solid form to give a S-B mixture in a liquid form in which sodium chloride and sodium bicarbonate are dissolved, and mix the liquid S-B mixture with the agent A.

11. The method for operating a dialysis fluid preparation apparatus according to claim 10, wherein the agent S in an aqueous solution form has a sodium chloride concentration of 8 to 14 g/100 ml.

12. The method for operating a dialysis fluid preparation apparatus according to claim 8, wherein the agent A contains an electrolyte components mixture other than sodium chloride and sodium bicarbonate.

13. A preparation method of dialysis fluid comprising a step of mixing an agent S containing sodium chloride, an agent B containing sodium bicarbonate, and an agent A containing electrolyte components other than sodium chloride and sodium bicarbonate, in the step, a ratio between amounts of the agent S and the agent B is adjusted during dialysis based on a dialysis fluid data set according to a disease state of a patient before actual start of dialysis, so as to change a bicarbonate ion concentration and to maintain a sodium ion concentration at a constant level in the dialysis fluid, wherein the disease state of the patient before start of dialysis comprises metabolic acidosis.

14. The preparation method of dialysis fluid according to claim 13, wherein the agent A contains an electrolyte components mixture other than sodium chloride and sodium bicarbonate.

* * * * *

UNITED STATES PATENT AND TRADEMARK OFFICE
CERTIFICATE OF CORRECTION

PATENT NO. : 9,463,266 B2
APPLICATION NO. : 13/728257
DATED : October 11, 2016
INVENTOR(S) : Hiroshi Noguchi et al.

It is certified that error appears in the above-identified patent and that said Letters Patent is hereby corrected as shown below:

On the Title Page

Item (73), Line 1, please change "Pharmaceuticals" to --Pharmaceutical--.

Signed and Sealed this
Fifth Day of June, 2018

Andrei Iancu
*Director of the United States Patent and Trademark Office*